(12) United States Patent
Scherzer et al.

(10) Patent No.: US 8,697,680 B2
(45) Date of Patent: Apr. 15, 2014

(54) NAPHTHOQUINONE DERIVATIVES USEFUL FOR PREVENTION OF AMYLOID DEPOSITS AND TREATMENT OF DISEASES INVOLVING AMYLOIDOGENESIS

(75) Inventors: Roni Scherzer, Tel Aviv (IL); Ehud Gazit, Ramat Hasharon (IL); Daniel Segal, Rehovot (IL)

(73) Assignee: Ramot At Tel Aviv University Ltd., Tel Aviv (IL)

(*) Notice: Subject to any disclaimer, the term of this patent is extended or adjusted under 35 U.S.C. 154(b) by 9 days.

(21) Appl. No.: 13/062,067

(22) PCT Filed: Sep. 6, 2009

(86) PCT No.: PCT/IL2009/000867
§ 371 (c)(1),
(2), (4) Date: May 27, 2011

(87) PCT Pub. No.: WO2010/026592
PCT Pub. Date: Mar. 11, 2010

(65) Prior Publication Data
US 2011/0224184 A1    Sep. 15, 2011

Related U.S. Application Data

(60) Provisional application No. 61/183,089, filed on Jun. 2, 2009.

(30) Foreign Application Priority Data

Sep. 5, 2008  (GB) ................................. 0816269.5

(51) Int. Cl.
| | |
|---|---|
| A61K 31/395 | (2006.01) |
| A61K 31/405 | (2006.01) |
| A61K 31/40 | (2006.01) |
| A61K 31/24 | (2006.01) |
| A61K 31/135 | (2006.01) |
| A61P 25/00 | (2006.01) |
| A61P 25/16 | (2006.01) |
| A61P 25/28 | (2006.01) |
| A61P 3/10 | (2006.01) |
| C07C 211/54 | (2006.01) |
| C07C 229/66 | (2006.01) |
| C07D 245/04 | (2006.01) |

(52) U.S. Cl.
USPC ........... 514/183; 514/419; 514/429; 514/535; 514/658; 540/471; 548/496

(58) Field of Classification Search
USPC .......... 514/183, 419, 429, 535, 658; 540/471; 548/496
See application file for complete search history.

(56) References Cited

U.S. PATENT DOCUMENTS

| | | | |
|---|---|---|---|
| 5,654,321 | A | 8/1997 | Moon et al. |
| 6,379,666 | B1 * | 4/2002 | Tobinick ............... 424/134.1 |
| 2005/0107472 | A1 | 5/2005 | Wischik et al. |

FOREIGN PATENT DOCUMENTS

| | | |
|---|---|---|
| JP | 54119027 A | 9/1979 |
| JP | 08113555 A | 5/1996 |
| JP | 2007145840 A | 6/2007 |
| KR | 0135034 B1 | 4/1998 |
| WO | 97/21432 A1 | 6/1997 |
| WO | 02/076939 A2 | 10/2002 |
| WO | 03/007933 A1 | 1/2003 |
| WO | 2005/053609 A2 | 6/2005 |
| WO | 2006/011136 A2 | 2/2006 |

OTHER PUBLICATIONS

Barghorn, Stefan et al., (2005) Globular amyloid beta-peptidel-42 oligomer—a homogenous and stable neuropathological protein in Alzheimer's disease. J Neurochem 95:834-847.
Bevins, Rick A. and Besheer, Joyce (2006) Object recognition in rats and mice: a one-trial non-matching-to-sample learning task to study 'recognition memory'. Nat Protoc 1(3):1306-1311.
Clark, Nigel G. (1985) The fungicidal activity of substituted 1,4-naphthoquinones. Part III: amino, anilino and acylamino derivatives. Pesticide Science 16:23-32.
Crowther, D. C. et al., (2005) Intraneuronal Abeta, non-amyloid aggregates and neurodegeneration in a Drosophila model of Alzheimer's disease. Neuroscience 132:123-135.
Gazit, Ehud (2002) the "Correctly Folded" State of Proteins: Is It a Metastable State? Angew Chem Intl Ed 41 (2):257-259.
Hodnett, Ernest M. et al., (1983) Substituted 1,4-naphthoquinones vs. The ascitic sarcoma 180 of mice. J Med Chem 26(4):570-574.
Ikeda, Nisaburo (1955) Antibacterial properties of 2- and 2,3-substituted 1,4-naphthoquinones. VI. Antibacterial effects of alkyl(aryl)amino-1,4-naphthoquinones. Yakugaku Zasshi (Journal of the Pharmaceutical Society of Japan) 75 (6):649-652 article in Japanese with English summary.
Kapadia, Govind J.et al., (1997) Antitumor promoting effects of naphthoquinone derivatives on short term Epstein-Barr early antigen activation assay and in mouse skin carcinogenesis. Cancer Lett 113:47-53.
Kapadia, Govind J.et al., (2001) Aminonaphthoquinones—a novel class of compounds with potent antimalarial activity against Plasmodium Falciparum. Pharmacol Res 43(4):363-367.
Kim, Hee et al., (2005) Effects of naturally occurring compounds on fibril formation and oxidative stress of beta-amyloid. J Agric Food Chem 53(22):8537-8541.

(Continued)

Primary Examiner — San-Ming Hui
Assistant Examiner — Kathrien Cruz
(74) Attorney, Agent, or Firm — Rothwell, Figg, Ernst & Manbeck, P.C.

(57) ABSTRACT

The present invention provides pharmaceutical compositions comprising substituted 1,4 naphthoquinones that are effective in preventing oligomerization of beta amyloid and subsequent pathologies associated with amyloid fibrils. These compositions are useful for the treatment of disease involving amyloidogenesis including neurodegenerative diseases such as Alzheimer's Disease or senile dementia. Particularly effective compositions comprise 1,4 naphthoquinones substituted with an amino acid residue selected from a heterocyclic or aromatic amino acid.

19 Claims, 13 Drawing Sheets

(56) References Cited

OTHER PUBLICATIONS

Lesne, Sylvain et al., (2006) A specific amyloid-beta protein assembly in the brain impairs memory. Nature 440:352-357.

Pannu Ravinder and Singh, Inderjit (2006) Pharmacological strategies for the regulation of inducible nitric oxide synthase: Neurodegenerative versus neuroprotective mechanisms. Neurochem Int 49:170-182.

Pawar, Amol P. et al., (2005) Prediction of "Aggregation-prone" and "Aggregation-susceptible" Regions in Proteins Associated with Neurodegenerative Diseases. J Mol biol 350:379-392.

Pisani, David E.et al., (1986) Relationship between inhibition of mitochondrial respiration by naphthoquinones, their antitumor activity, and their redox potential. Biochemical Pharmacology 35(21):3791-3798.

Porat, Yair et al., (2004) Inhibition of islet amyloid polypeptide fibril formation: a potential role for heteroaromatic interactions. Biochemistry 43(45):14454-14462.

Porat, Yair et al., (2006) Inhibition of Amyloid Fibril Formation by Polyphenols: Structural similarity and aromatic interactions as a common inhibition mechanism. Chem Biol Drug Des 67:27-37.

Ritchie, Craig W. et al., (2003) Metal-protein attenuation with iodochlorhydroxyquin (clioquinol) targeting Abeta amyloid deposition and toxicity in Alzheimer disease: a pilot phase 2 clinical trial. Arch Neurol 60:1685-1691.

Shrestha-Dawadi, Prativa Bade et al., (1996) on the synthesis of naphthoquinonyl heterocyclic amino acids. Synthesis 12:1468-1472.

Yu, Sheu M. et al., (1997) Inhibition of nitric oxide synthase expression by PPM-18, a novel anti-inflammatory agent, in vitro and in vivo. Biochem J 328:363-369.

International Search Report of PCT/IL2009/000867 mailed Jan. 18, 2010, 4 pages.

Search Report of GB Patent Appln. No. 0816269.5 dated Jan. 7, 2009, 1 page.

WPI abstract accession No. 2007-443218 [43] & JP 2007145840 Digital Biotech Co ltd, 16 pages.

Roushdi et al., (1976) Synthesis of some quinones of potential therapeutic interest. Acta Pharmaceutica Jugoslavica 26(4): 287-294.

Ryu et al., (1992) Antibacterial and antifungal activities of 1,4-naphthoquinone derivatives. Yakhak Hoechi (Journal of the Pharmaceutical Society of Korea) 36(2): 110-114—Translated abstract.

* cited by examiner

NAPHTHOQUINONE DERIVATIVES USEFUL FOR PREVENTION OF AMYLOID DEPOSITS AND TREATMENT OF DISEASES INVOLVING AMYLOIDOGENESIS

CROSS REFERENCE TO RELATED APPLICATIONS

This application is a 35 U.S.C. §371 National Phase Entry Application from PCT/IL2009/000867, filed Sep. 6, 2009, and designating the United States, which claims priority under 35 U.S.C. §119 to British Application No. 0816269.5, filed Sep. 5, 2008, and claims the benefit of U.S. Provisional Patent Application No. 61/183,089, filed on Jun. 2, 2009, the entire disclosures of which are incorporated herein in their entireties.

FIELD OF THE INVENTION

The present invention provides pharmaceutical compositions comprising naphthoquinone derivatives that are effective in preventing oligomerization of amyloid proteins including but not limited to beta amyloid, and subsequent pathologies associated with amyloid fibrils. These compositions are useful for the treatment of diseases involving amyloidogenesis including neurodegenerative diseases such as Alzheimer's Disease or senile dementias.

BACKGROUND OF THE INVENTION

Amyloids are filamentous protein deposits in sizes ranging from nanometers to microns which are composed of aggregated peptide β-sheets formed from parallel or anti parallel alignments of peptide β-strands. Amyloid fibril formation has attracted a great deal of recent attention due to their association with a large number of major human diseases, including Alzheimer's Disease, Huntington's Disease, Parkinson's Disease, Creutzfeldt-Jakob disease, prion disorders, amyotrophic lateral sclerosis (ALS, Lou Gehrig's disease) and Type II diabetes (Gazit et al., Angew Chem Intl Ed., 2002, vol. 114: p. 267-269).

Quinones are compounds which include a non aromatic ring and two carbonyl groups at, e.g., the 1,4 or the 1,2 position to one another. The three basic most common quinones are benzoquinones, naphthoquinones and anthraquinones (FIG. 1).

A variety of quinones are known to act as inhibitors of various metabolic pathways in the cell, and many types of quinones are used in the field of medicinal chemistry. Both natural and designed synthetic quinones are known as antibacterial, anti-viral, and also anti-cancer agents.

WO 97/21432 discloses the use of bicylic mono- or diketone derivatives as drugs for treating inflammation, migraine and shock. WO 2006/011136 discloses naphthoquinone derivatives and their use for treating cardiovascular disease and malignancies. WO 2006/011136 relates to the use of naphthoquinone derivatives that modulate the activity of protein kinases, and use of the derivatives in pharmaceutical compositions for treating disorders associated with MAPKs signaling, ERKs signaling, p38 signaling, and JNKs signaling.

Certain quinones have been reported to reduce neurotoxicity related to β-amyloid proteins, including danthron (1,8-dihydroxyanthraquinone; Ritchie et al., 2003, Arch Neurol. vol. 60: p. 1685-1691), naphthoquinone compound selected from naturally existing juglone, 5,8-hydroxy-1,4-naphthoquinone and 1,2-naphthoquinone (JP 2007145840) and Vitamin K-type compounds (WO 03/007933 and US 2005/0107472). However, these quinones are not substituted by an amine group.

Increasing evidence supports the fundamental role of early soluble species of the beta amyloid protein (Aβ) in the pathogenesis and neurotoxicity of Alzheimer's Disease (AD). It has been established that these amyloidogenic peptides and proteins ultimately cause the synaptic lose and dementia associated with Alzheimer's Disease. While there is growing recognition that the early oligomer intermediates and not the fibrils are the most toxic amyloid forms, the molecular mechanism underlying the misfolding and assembly of amyloid proteins is not fully understood. Since these structures self-assemble from monomers into higher oligomeric or fibrillar structures in a highly ordered and efficient manner, it is likely that specific molecular recognition elements mediate this process.

Nowhere in the background art was it taught or suggested that 3-amino-1,4-naphthoquinones could serve as inhibitors of the process of formation of beta amyloid oligomers and fibrils (Aβ). There is an unmet medical need for small non-toxic organic molecules capable of penetrating the central nervous system and preventing oligomerization of beta amyloid and other amyloid type proteins involved in neurological diseases and subsequent pathological fibril formation.

SUMMARY OF THE INVENTION

The present invention provides pharmaceutical compositions designed to target the early steps of the molecular recognition and structural transition leading to the formation of the toxic oligomeric or fibrillar species of amyloidogenic peptides and proteins.

The compositions and methods of the present invention utilize 3-amino 1,4-naphthoquinone compounds having low toxicity, good bioavailability and adequate penetration through the blood brain barrier. Some of the compounds are novel compounds and are claimed as such.

The present invention is based in part on the unexpected discovery that 3-amino-1,4-naphthoquinone derivatives are effective in preventing oligomerization of amyloid proteins. Moreover, the pharmaceutical compositions of the present invention exhibit particularly high affinity to β-amyloid and exceptional inhibitory effect on the formation of oligomers and mature fibrils of the β-amyloid. As exemplified hereinbelow, the efficiency of the inhibitors of the present invention is higher than the efficiency of other napthoquinone derivatives.

The inventors of the present invention and others previously identified the key role of aromatic amino acid residues in the molecular recognition and self-assembly processes that lead to the formation of various amyloid assemblies. It has been found that the amyloidogenic potential of aromatic residues is significantly higher than that of aliphatic amino acids. The inventors have now discovered that targeting the aromatic recognition interfaces using small aromatic molecules, specifically 3-amino-1,4-naphthoquinones, is a useful method in inhibiting the early steps of amyloid formation.

According to a first aspect the present invention provides pharmaceutical compositions comprising substituted 3-amino-1,4-naphthoquinones for prevention of amyloid oligomerization and fibril formation. According to some embodiments the pharmaceutical compositions comprise as an active ingredient a compound having the general formula (I):

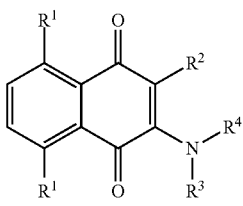

(I)

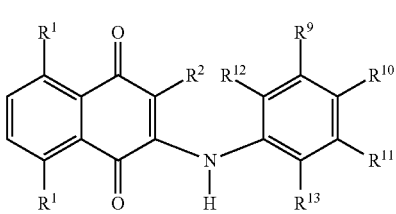

(II)

wherein
each $R^1$ is independently selected from H and OH;
$R^2$ is selected from H, a halogen and —$NR^5R^6$ wherein $R^5$ and $R^6$ are each independently H, a saturated or unsaturated cyclic moiety comprising from 5 to 8 atoms, an unsubstituted or substituted aryl (e.g., phenyl), or $R^5$ and $R^6$ may together form a saturated or unsaturated heterocyclic moiety comprising from 5 to 8 atoms;
$R^3$ is selected from H, an amino acid side chain, an amino acid residue, —$C(O)CH_3$, an unsubstituted or substituted aryl, an unsubstituted or substituted heteroaryl and —$CHR^7(CH_2)_n CH_2R^8$ wherein n=0, 1, 2 or 3, $R^7$ is selected from H and —COOH, and $R^8$ is selected from H, —COOH, —$SO_3H$, 2-indolyl, 3-indolyl, an unsubstituted or substituted aryl and an unsubstituted or substituted heteroaryl; and
$R^4$ is H; or when $R^2$ is —$NR^5R^6$, $R^2$ and $R^4$ may together form a saturated or unsaturated heterocylic moiety comprising from 5 to 8 atoms.

In one preferred embodiment, $R^2$ is a halogen, such as Cl. In another preferred embodiment, $R^2$ is H. According to other preferred embodiments, $R^2$ is $NR^5R^6$ wherein $R^5$ is H and $R^6$ is an unsubstituted or substituted aryl (e.g., phenyl). According to yet other preferred embodiments, $R^5$ and $R^6$ together form a saturated or unsaturated heterocyclic moiety comprising from 5 to 8 atoms.

According to certain preferred embodiments of the present invention, $NR^3R^4$ represents an amino acid residue bound to the quinone moiety through the amino group of the amino acid. According to some embodiments the amino acid is a heterocyclic amino acid selected from tryptophan, histidine and proline. According to other embodiments the amino acid is an aromatic amino acid selected from tyrosine and phenyalanine. According to certain currently preferred embodiments of the present invention $NR^3R^4$ is a tryptophan residue. According to some other embodiments, the amino acid is a non natural amino acid. For example, according to a currently preferred embodiment, $NR^3R^4$ is α-aminoisobutyric acid (AIB).

According to other preferred embodiments of the present invention, $R^3$ represents or comprises an amino acid side chain. According to some embodiments, $R^3$ comprises or represents a heterocyclic amino acid side chain selected from the side chains of tryptophan, histidine and proline. According to other embodiments $R^3$ comprises or represents an aromatic amino acid side chain selected from the side chains of tyrosine and phenyalanine. According to certain currently preferred embodiments of the present invention $R^3$ comprises or represents tryptophan side chain.

According to specific embodiments the compounds of Formula (I) include pharmaceutically acceptable salts and solvates. According to additional embodiments the compounds include either isolated optically active isomers or mixtures thereof.

According to certain embodiments the pharmaceutical compositions comprise as an active ingredient a compound having the general formula (II):

wherein $R^1$ and $R^2$ are as defined above, and
$R^9$, $R^{10}$, $R^{11}$, $R^{12}$ and $R^{13}$ are each independently selected from H, halogen, $C_1$-$C_4$ linear or branched alkyl, $NO_2$, styrenyl, —$C(O)OR^{14}$, —$OR^{15}$ or $NR^{16}R^{17}$ where $R^{14}$, $R^{15}R^{16}$ and $R^{17}$ are independently selected from H and a $C_1$-$C_4$ linear or branched alkyl.

According to some embodiments, the pharmaceutical composition comprises as an active ingredient a compound selected from the group consisting of:

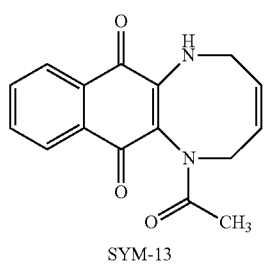

SYM-13

III

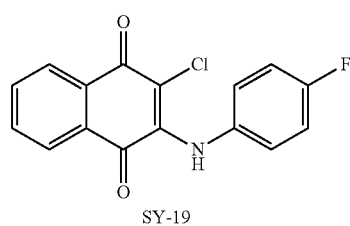

SY-19

IV

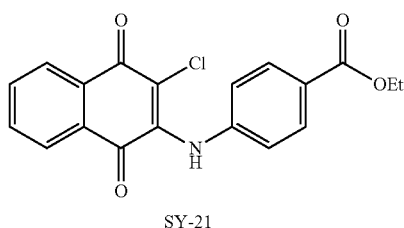

SY-21

V

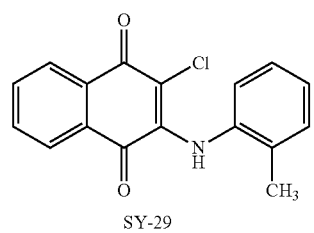

SY-29

VI

-continued
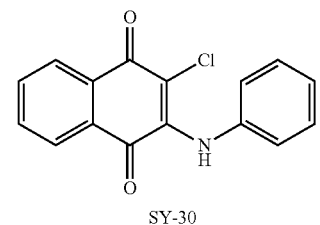
SY-30
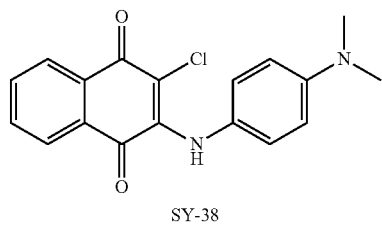
SY-38
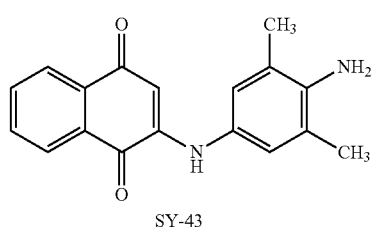
SY-43
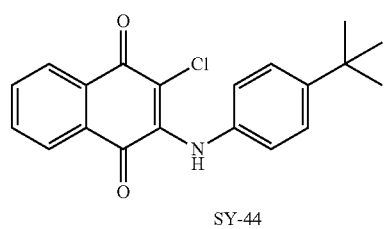
SY-44
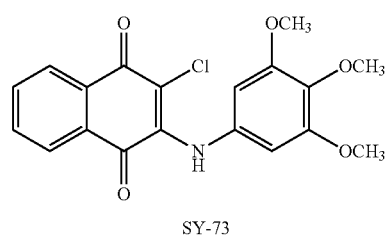
SY-73
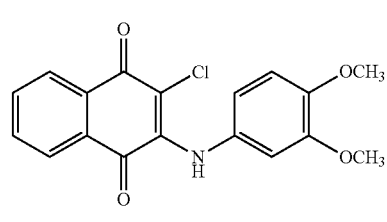
SY-74
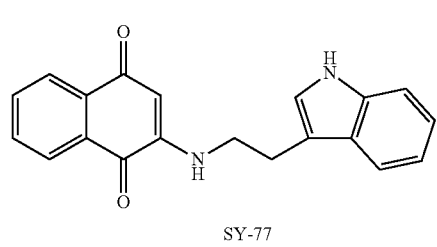
SY-77
-continued
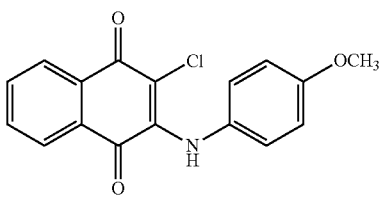
SY-78
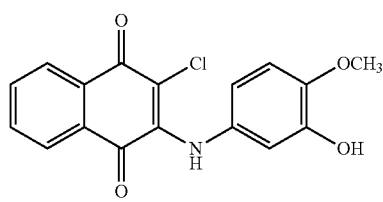
SY-79
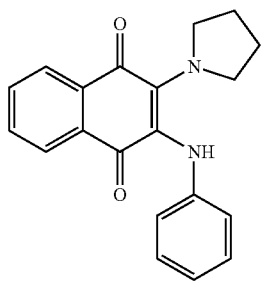
SY-80
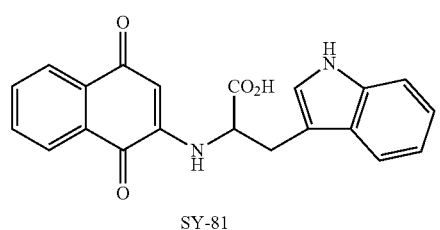
SY-81
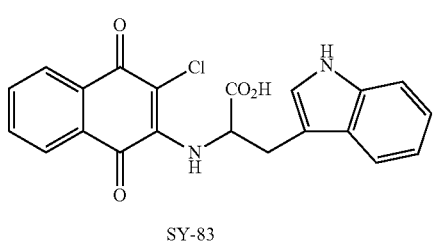
SY-83

-continued

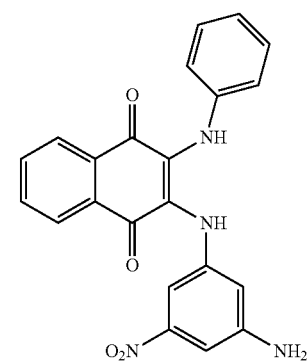

SY-85

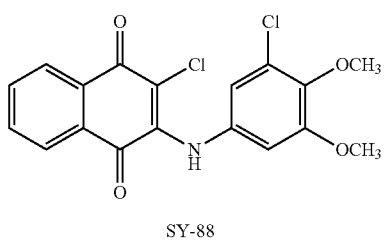

SY-88

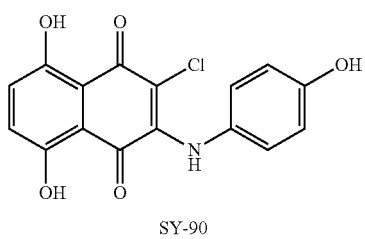

SY-90

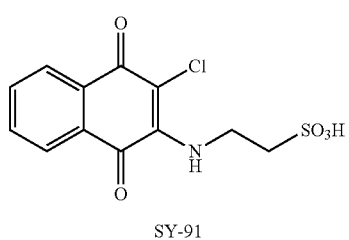

SY-91

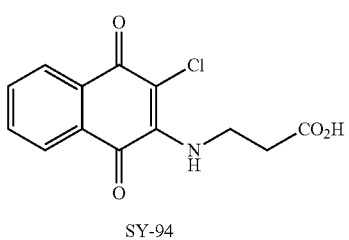

SY-94

XIX

XX

XXI

XXII

XXIII

-continued

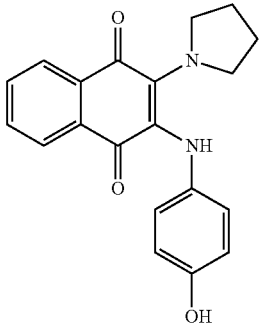

SY-96 and

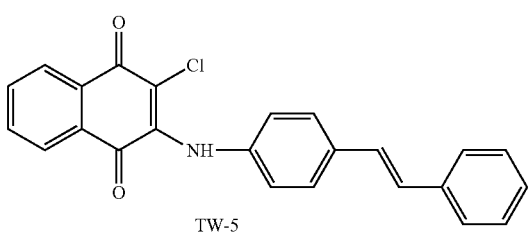

TW-5

XXIV

XXV

Some of the compounds are new and are claimed as such.

The compositions of the present invention are inhibitors of amyloidogenesis. One embodiment of amyloidogenesis is beta amyloid oligomerization and fibril formation as is associated with Alzheimer's Disease and senile dementias. The examples described hereinbelow, in vitro in cultured cells and in the intact organism, indicate that the substituted 1,4 naphthoquinones of the invention are potent inhibitors of Alzheimer's Disease-associated beta amyloid (Aβ) oligomers and fibrils.

Surprisingly, as exemplified hereinbelow in a model system, the compounds of the invention exhibit a significant inhibitory effect on characteristic clinical symptoms associated with Alzheimer's Disease, specifically, memory impairment and loss of cognitive functioning.

Thus, according to another aspect the present invention provides methods of treating a disease related to amyloidogenesis in an individual in need thereof comprising administering to the individual a pharmaceutical composition comprising as an active ingredient a 1,4 naphthoquinone derivative of formula I, as defined hereinabove, capable of inhibiting the oligomerization and deposition of filamentous proteins. According to specific embodiments the active ingredient is an amino acid derivative of a 1,4 naphthoquinone. According to certain embodiments the amino acid is a heterocyclic, aromatic or a hydrophobic amino acid. According to specific embodiments the amino acid is selected from tryptophan, tyrosine, histidine, proline, phenylalanine and α-aminoisobutyric acid. According to particular embodiments the amino acid is tryptophan.

According to certain embodiments the disease related to amyloidogenesis is Alzheimer's Disease. According to further embodiments, the pharmaceutical composition inhibits or reduces symptoms associated with Alzheimer's Disease selected from memory impairment and loss of cognitive functioning.

It is to be understood explicitly that the compounds, compositions and methods of the invention will be applicable to other diseases where the pathology involves amyloidogenesis. It is envisaged that the disclosed compositions comprising naphthoquinone derivative compounds will be effective against various amyloid-associated diseases, in humans and in domestic animals, including but not limited to: Alzheimer's disease, Huntington's chorea, Parkinson's disease, Creutzfeldt-Jakob disease, prion disorders, amyotrophic lateral sclerosis (ALS, Lou Gehrig's disease) and Type II diabetes.

The present invention further encompasses 3-amino-1,4-naphthoquinones derivatives of formula (I) or (II) which are claimed as such and form one embodiment of the present invention.

The present invention will be more fully understood from the following figures and detailed description of the preferred embodiments thereof.

DETAILED DESCRIPTION OF THE INVENTION

Figure 1:
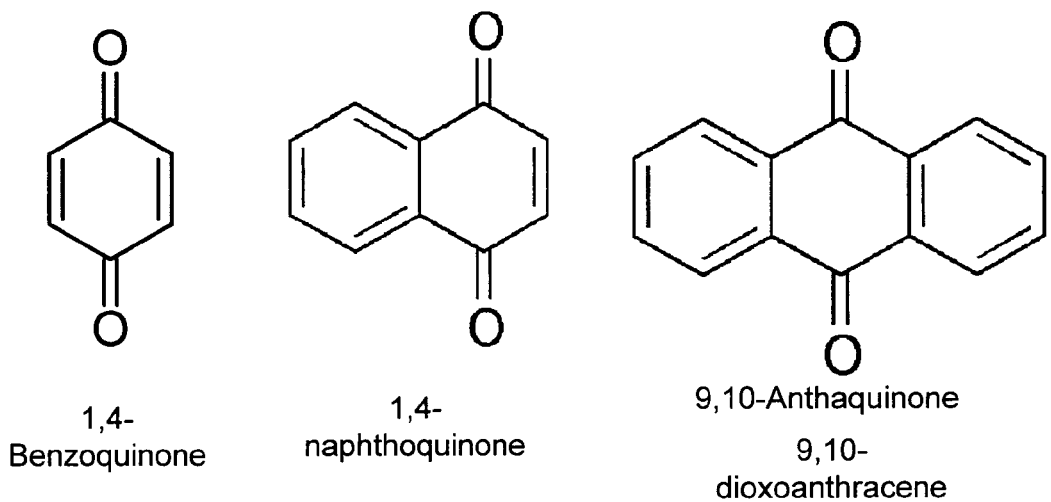
FIG. 1 shows basic structure of common quinones.

The present invention discloses pharmaceutical compositions comprising a 3-amino-1,4-napthoquinone. The present invention further provides methods for targeting the early steps of the molecular recognition and structural transition leading to the formation of the toxic oligomeric or fibrillar species of amyloid forming proteins, thereby inhibiting the formation of amyloid oligomers and fibrils.

Amyloid commonly refers to extracellular deposits of protein fibrils with a characteristic appearance in the electron microscope, a typical X-ray diffraction pattern and affinity for Congo red with concomitant green birefringence.

Amyloid fibril formation is associated with many diseases, including Alzheimer's, Huntington's, Parkinson's, Creutzfeldt-Jakob disease, prion disorders, amyotrophic lateral sclerosis (ALS, Lou Gehrig's disease) and Type II diabetes (Gazit et al., ibid). Each of these disease is associated with amyloid fibrillar deposits though the specific proteins are different in each case.

Alzheimer's Disease (AD) is the most common cause of dementia among older people. Dementia is the loss of cognitive functioning, namely, thinking, remembering, and reasoning, to such an extent that it interferes with a person's daily life and activities. According to recent estimates, as many as 2.4 to 4.5 million Americans are living with AD. AD is irreversible, and it progressively destroys memory and thinking skills, and eventually even the ability to carry out the simplest tasks. The specific amyloid protein associated with AD is termed beta amyloid.

Though there is no specific sequence homology between the proteins associated with each one of these diseases, they are all thought to involve important conformational changes in proteins, termed misfolding, that usually produce β-sheet structures with a strong tendency to aggregate into water-insoluble fibrous polymers. In each of the various diseases, a different endogenous protein self-assembles into highly ordered fibrillar structures. Due to the pathological effect of the process and the severity of the amyloid-related diseases, much effort has been directed towards elucidating and preventing the amyloidogenic process, though its molecular mechanism is not yet fully understood. The spontaneous formation of amyloid fibrils from misfolded peptides is often discussed as a version of a nucleated growth polymerization pathway. In this mechanism, the overall rate of amyloid formation is limited by the slow generation of nuclei (the nucleation phase), which, once formed, rapidly grow by monomer addition to the fibril ends (the elongation phase). The fibrils usually consist of a number (typically 2-6) of protofilaments, each about 2-5 nm in diameter. These protofilaments twist together to form ropelike fibrils that are typically 7-13 nm wide or associate laterally to form long ribbons that are 2-5 nm thick and up to 30 nm wide. X-ray fiber diffraction data have shown that in each individual protofilament the protein or peptide molecules are arranged so that the polypeptide chain forms β-strands that run perpendicular to the long axis of the fibril.

Although the specific etiologies of amyloidogenic diseases are not fully understood, it has recently been demonstrated that the intermediate soluble aggregated states (oligomers), rather than the precipitated insoluble polymeric (fibrillar/plaque) aggregates, are the most toxic and may be the source of pathology and aberrant physiology in amyloid diseases. The neurological disruptive nature of the oligomers was established in various models. Experimentally generated oligomers applied to brain slices or injected in vivo resulted in failure of hippocampal long-term potentiation (LTP), which is a form of synaptic information storage loss, well-known as a paradigm for memory mechanism disorders. It is not yet clear whether these soluble oligomers are formed as intermediates in the pathway that eventually leads to the non soluble fibrils and plaques ("on-pathway") or formed in a mechanism distinct from the pathway to fibrillization ("off pathway").

Since many of the amyloid-associated diseases are correlated with advanced age, it seems likely they will become a major public health concern due to gradual increase in life expectancy. Therefore, great effort has been put into understanding the mechanism of these diseases and to finding therapeutic treatments for them. Different mechanisms were postulated for the cytotoxic effects of amyloidogenic polypeptides, including (i) interfering with cell membrane by forming membrane pores or by penetration of fibrils to the membrane and destabilizing it; (ii) interfering with cellular pathways by inducing oxidative stress, loss of function of proteins (due to aggregation), or hyper phosphorylation of proteins; (iii) other indirect mechanisms that can end up in cell apoptosis. Therapeutics strategies can target the cellular mechanism influenced or, more directly, the amyloid assemblies and the factors that contribute to their formation. It appears that a most promising direction for developing therapeutic agents to treat Alzheimer's Disease (AD) and other amyloid-associated diseases is by targeting the early molecular recognition and self-assembly processes rather than breaking the mature amyloid fibrils that have already been formed.

An approach that has gained attention in recent years is the use of small molecules as inhibitors of the process of amyloid fibril formation. One major advantage of this approach is that small molecules are good candidates for drug development, they can be administrated orally and can penetrate cell membranes and traverse the blood-brain barrier relatively easily. The first observations that gave rise for the search for small molecules that can inhibit amyloid fibril formation are experiments showing that the amyloid dye Congo red can inhibit the fibrillization process. Since then dozens of small molecules were tested for their ability to inhibit the process of amyloid fibril formation in vitro and to have protective effect in cell culture assays, some molecules gave promising results while others gave negative results. A very interesting property common to this wide group of small molecules that are inhibitors of amyloid deposits is their aromatic nature (Porat et al., Chem. Biol. Drug Des., 2006, vol. 67:27-37). Several of these small aromatic molecules were tested with various amyloidogenic proteins and were shown to be generic inhibitors of the fibril formation process (Porat et al. 2006, ibid). Taken together with the role of the aromatic interaction occurring in amyloid formation described below, these findings point to a potential generic mechanism for inhibition of amyloid fibril formation, namely, by targeting the aromatic moieties of the amyloidogenic peptides with small aromatic molecules. While these small molecules have been implicated in inhibition the large fibrils they might also turn out to be capable of inhibiting the accumulation of the soluble oligomers.

Aromatic interactions are made up of a combination of forces including electrostatic, hydrophobic and Van der Waals interactions. This interaction between molecules containing aromatic residues is often referred to as aromatic (π-π) stacking or aryl stacks. These are non-covalent interactions involving attraction between planar aromatic rings. Generally, aromatic interactions depend upon charge distribution and also the shape of molecule and are governed by geometrical requisites. The geometries have been proposed on the basis of the electrostatic component of the interaction. They can be parallel displaced, T-shaped, parallel staggered or herringbone. Interactions are caused by intermolecular overlapping of π-orbitals in π conjugated systems, so they become stronger as the number of π electron increases. Aromatic interactions are found to play a role in self assembly processes and believed to provide selectivity as well as stability. Base stacking has been proposed to stabilize the helical structures of DNA and RNA, and aromatic residues in proteins were found to play key roles in recognizing DNA and RNA. In addition to participating in recognition, aromatic residues have been found to stabilize protein structures through clusters and tertiary contacts. Isolated motifs of secondary structure of proteins have also been shown to benefit from presence of aromatic residues. Different studies have proposed that aromatic interactions may be driven by gain in enthalpy, or entropy.

The wide use of quinones in the medicinal industry, and in particular the reported effect of an anthraquinone on β-amyloid toxicity, their aromatic nature and their resemblance to several known small molecules that can inhibit the fibril formation of various proteins, make them worthy candidates for their potential in preventing or slowing the progression of Alzheimer's Disease and other disease that may involve amyloidogenesis.

While there is growing recognition that the early oligomer intermediates and not the fibrils are the most toxic amyloid forms, the molecular mechanism underlying the misfolding and assembly of amyloid proteins is not fully understood. Since these structures self-assemble from monomers into higher oligomeric or fibrillar structures in a highly ordered and efficient manner, it is likely that specific molecular recognition elements mediate this process. Thus, the strategy taken by inventors of the present invention was to target the very early steps of the molecular recognition and structural transition leading to the formation of the toxic oligomeric or fibrillar species. The inventors and others previously identified the key role of aromatic residues in the molecular recognition and self-assembly processes that lead to the formation of various amyloid assemblies. Indeed, the amyloidogenic potential of aromatic residues is significantly higher than that of aliphatic amino acids. Thus, the inventors suggested that targeting the aromatic recognition interfaces using small aromatic molecules, specifically 3-amino-1,4-napthoquinone, would be highly useful in inhibiting the very early steps of amyloid formation (Porat et al., Biochemistry, 2004, vol. 43:14454-14462).

The present invention has been exemplified using beta amyloid as an embodiment of amyloid protein oligomers exploiting a protocol for the formation of SDS-stable Aβ oligomers (Barghorn et al., J. Neurochemistry, 2005, vol. 3:834-847). As inhibitors the present invention utilized molecules based on the structure of quinones. A variety of quinones are known to act as inhibitors of various metabolic paths in the cell, to have antibacterial and anti-viral capabilities and also to be anti-cancer agents. Various quinones have also shown to reduce neurotoxicity related to β-amyloidproteins.

According to the present invention, for the first time pharmaceutical compositions comprising 3-amino-1,4-napthoquinones represented by formula I were shown to be particularly useful in inhibiting the early steps of the molecular recognition and structural transition leading to the formation of the toxic oligomeric or fibrillar species. Accordingly, pharmaceutical composition comprising the 1,4 naphtoquinone derivative represented by formula I, are exceptionally useful in inhibiting diseases associated with formation of the toxic oligomeric or fibrillar species, such as Alzheimer's Disease.

Without wishing to be bound by any theory or mechanism, the inventors of the present invention suggest that the aromatic core of the 3-amino-1,4-napthoquinone of the invention participates in the hetero-aromatic interactions required for specific molecular recognition between small molecules and amyloid assemblies, and the substituted side chain induces a steric effect on the stacking of the monomeric subunits of the amyloid. A specific embodiment of the present invention is beta-amyloid.

It is to be understood explicitly that the compounds, compositions and methods of the invention will be applicable to other diseases where the pathology involves amyloidogenesis. It is envisaged that the disclosed compositions comprising the naphthoquinone derivative compounds of the invention will be effective against various amyloid-associated diseases, in humans and in domestic animals, including but not limited to: Alzheimer's Disease, and other dementias, Huntington's Chorea, Parkinson's Disease, Creutzfeldt-Jakob disease, prion disorders, amyotrophic lateral sclerosis (ALS, Lou Gehrig's disease) and Type II diabetes.

According to certain embodiments the compositions of the invention comprise as an active ingredient a compound of the general formula (I). According to specific embodiments the compound of general formula (I) is an amino acid derivative of a 1,4 naphthoquinone.

According to specific embodiments the compound of general formula (I) comprises an amino acid side chain.

According to some embodiments the compound of general formula (I) comprises a heterocyclic amino acid side chain selected from the group consisting of the side chains of tryptophan, histidine and proline. According to other embodiments the compound of general formula (I) comprises an aromatic amino acid side chain selected from the group consisting of the side chains of tyrosine and phenylalanine. According to certain currently preferred embodiments of the present invention the compound of general formula (I) comprises a side chain of tryptophan amino acid residue.

Chemical Definitions

An "alkyl" group refers to any saturated aliphatic hydrocarbon. The alkyl group may be linear or branched. Preferred are alkyl groups containing from 1 to 4 carbon atoms ($C_1$-$C_4$ alkyl). Examples of saturated alkyl groups include but are not limited to methyl, ethyl, n-propyl, isopropyl, n-butyl, isobutyl, sec-butyl, tert-butyl, amyl, tert-amyl, hexyl, heptyl, octyl, nonyl, decyl, undecyl, dodecyl and the like. The alkyl group can be unsubstituted, or substituted with one or more substituents selected from the group consisting of halogen, hydroxy, alkoxy, aryloxy, alkyl, alkylaryloxy, heteroaryloxy, oxo, styrenyl, cycloalkyl, phenyl, heteroaryl, heterocyclyl, naphthyl, amino, alkylamino, arylamino, heteroarylamino, dialkylamino, diarylamino, alkylarylamino, alkylheteroarylamino, arylheteroarylamino, acyl, acyloxy, nitro, carboxy, carbamoyl, carboxamide, cyano, sulfonyl, sulfonylamino, sulfinyl, sulfinylamino, thiol, $C_1$ to $C_{10}$ alkylthio arylthio, or $C_1$ to $C_{10}$ alkylsulfonyl groups. Any substituent can be unsubstituted or further substituted with any one of these aforementioned substituents.

The term "saturated or unsaturated cyclic moiety", as used herein, encompasses cycloalkyl, heterocycloalkyl, aryl or heteroaryl moieties. In a preferred embodiment, the cyclic moiety comprises from 5 to 8 atoms. In another preferred embodiment, the cyclic moiety is an aryl as defined herein (e.g., a phenyl).

The term "cycloalkyl" used herein alone or as part of another group denotes any unsaturated or unsaturated (e.g., cycloalkenyl, cycloalkynyl) monocyclic or polycyclic group. Nonlimiting examples of cycloalkyl groups are cyclopropyl, cyclobutyl, cyclopentyl, cyclohexyl or cycloheptyl. Examples or cycloalkenyl groups include cyclopentenyl, cyclohexenyl and the like. The cycloalkyl group can be unsubstituted or substituted with any one or more of the substituents defined above for alkyl.

The term "aryl" as used herein alone or as part of another group refers to an aromatic ring system containing from 6-14 ring carbon atoms. The aryl ring can be a monocyclic or bicyclic. Non-limiting examples of aryl groups are phenyl, naphthyl, and the like. The aryl group can be unsubstituted or substituted through available carbon atoms with one or more groups defined above for alkyl.

The term "heteroaryl" as used herein alone or as part of another group refers to a heteroaromatic system containing at least one heteroatom ring wherein the atom is selected from nitrogen, sulfur and oxygen. The heteroaryl contains 5 or more ring atoms. The heteroaryl group can be monocyclic or bicyclic and the like. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. According to some preferred embodiments, the heteroaryl group is indoline (i.e., indolyl) such as 2-indolyl or 3-indolyl. The heteroaryl group can be unsubstituted or substituted through available atoms with one or more groups defined hereinabove for alkyl.

The term "hetereocyclyl", "heterocyclic moiety" or "heterocyclic ring" as used herein interchangeably refers to cyclic structures comprising one to four heteroatoms, such as oxygen, sulfur and/or nitrogen, in particular nitrogen, either alone or in conjunction with sulfur or oxygen ring atoms. Preferably, the heterocyclic moieties comprise five to eight atoms. These five-membered to eight-membered rings can be saturated, fully unsaturated or partially unsaturated. Preferred heterocyclic moieties include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, dihydrothiazolyl, and the like. The heterocyclyl group can be unsubstituted or substituted through available atoms with one or more groups defined hereinabove for alkyl.

An "amino" group refers to an $NH_2$ group.

The term "halogen" or "halo" as used herein alone or as part of another group refers to chlorine, bromine, fluorine, and iodine.

The term "amino acid" as used herein includes naturally occurring and synthetic α, β, λ, or γ amino acids, and includes but is not limited to, alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaroyl and histidinyl. Alpha-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, asparagine, and glutamine), arylalkyl (e.g., as in phenylalanine), substituted arylalkyl (e.g., as in tyrosine), heteroarylalkyl (e.g., as in tryptophan, histidine) and the like.

The term "amino acid residue" as used herein refers to a functional group derived from an amino acid which is attached to the quinone ring via the amino group (i.e., —NH—CH(R)—COOH wherein R is the amino acid side chain). Amino acids may generally be natural or non-natural synthetic amino acids. The amino acids may be of either L or D conformation, or they can be racemic. The amino acid residue may be selected from non-polar amino acids (such as alanine, leucine, isoleucine, valine, proline, phenylalanine, tryptophan and methionine) and polar amino acids which are uncharged at physiological conditions (such as serine, threonine, cysteine, tyrosine, asparagine, and glutamine).

The pharmaceutical compositions of the present invention contain in addition to the active ingredient conventional pharmaceutically acceptable carriers, diluents and the like.

The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic agent is administered. Carriers are more or less inert substances when added to a pharmaceutical composition to confer suitable consistency or form to the composition.

Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may be prepared for oral administration or for injection, the term including subcutaneous, transdermal, intravenous, intrathecal, and other parenteral routes of administration. The liquid compositions include aqueous solutions, with or without organic cosolvents, aqueous or oil suspensions, flavored emulsions with edible oils, as well as elixirs and similar pharmaceutical vehicles. In addition, the compositions of the present invention may be formed as aerosols, for intranasal and like administration.

The active dose for humans is generally in the range of from 0.005 mg to about 50 mg per kg body weight, in a regimen of 1-4 times a day. However, administration every two days may also be possible, as the drug has a rather prolonged action. The preferred range of dosage is from about 0.1 mg/kg to about 20 mg/kg body weight. Nevertheless, it is evident to the man skilled in the art that dosages would be determined by the attending physician, according to the disease to be treated, method of administration, patient's age, weight, contraindications and the like.

The compounds defined above are effective as inhibitors of amyloid peptide oligomerization and fibril deposition and as such can be used as active ingredients of pharmaceutical compositions for treatment of one, or simultaneously several, symptoms of the disorders defined above.

Having now generally described the invention, the same will be more readily understood through reference to the following examples, which are provided by way of illustration and are not intended to be limiting of the present invention.

EXAMPLES

The tryptophan naphthoquinones, SY-81 and SY-83, were synthesized according to the procedure described by Shrestha-Dawadi and co-workers (Synthesis, 1996, vol. 12, 1468-1472) starting from the appropriate naphthoquinone and tryptophan. Additional exemplary compounds were synthesized by methods disclosed in WO 2006/011136 and WO 97/21432.

Amyloid β-peptide(1-42) and amyloid β-peptide(1-40) trifluoroacetate salts ($A\beta_{1-42}$ and $A\beta_{1-40}$) were purchased from Bachem (Bubendorf, Switzerland).

Aβ intermediates and toxic oligomers were produced according to Barghorn et al. (ibid). To avoid pre-aggregation, synthetic lyophilized $A\beta_{1-42}$ was pretreated with HFIP. $A\beta_{1-42}$ was dissolved in 100% HFIP, sonicated for 20 seconds and incubated for 2 hours at 37° C. under shaking at 100 RPM. SY-81 and SY-83 were dissolved in DMSO to a concentration of 300 mM, sonicated for 1 min and then diluted in DMSO to the final concentrations. After evaporation in a speedvac, $A\beta_{1-42}$ was resuspended in DMSO (with or without SY-81 or SY-83) to 5 mM and diluted with 20 mM $NaH_2PO_4$, 140 mM NaCl, pH 7.4 to a final concentration of 400 μM and ⅒ volume 2% SDS (final concentration of 0.2%). The Aβ toxic oligomers were generated by a further dilution with two volumes of $H_2O$ and incubated for another 18 hours or more. Aβ aggregation products were then separated using a 15% Tris-Tricine gel and stained using Imperial protein stain.

For the florescence anisotropy studies SY-81 or SY-83 was dissolved in DMSO to a concentration of 1 μM and sonicated for 5 min. The solution was immediately mixed with aliquots of an API-42 stock solution (20 μM) to varying final polypeptide concentrations. SY-81 and SY-83 polarization measurements were carried out using an ISS K2 fluorimeter. The solutions were excited at 280 nm and emission was monitored at 350 nm. For each single point, at least five measurements were collected and their average values were used for the calculation. All experiments were performed in PBS (pH 7.4).

The cytotoxicity assay was performed with Rat PC12 cells (1.5×10⁵ cells/mL) cultured in 96-well microplates (100 μL/well) and incubated overnight at 37° C. Samples with toxic oligomers from above were either dialyzed over night against PBS buffer or diluted with 9 volumes of an aqueous solution containing 33% methanol and 4% acetic acid, and incubated for 2 hours at 4° C. The samples were then centrifuged at 16,000 g for 40 minutes, the supernatant discarded and the pellet was resuspended in 5 mM $NaH_2PO_4$, 35 mM NaCl, pH 7.4. To each well we added 100 μL of 0.5 μM Aβ which formed toxic oligomers and prepared mixtures of inhibitors at various concentrations. Each experiment was repeated four times. Following incubation for 24 hours at 37° C., cell viability was evaluated using the MTT assay. Briefly, 204 of 5 mg/mL MTT dissolved in PBS was added to each well. After 4 hours incubation at 37° C., 100 μL, of extraction buffer [20% SDS dissolved in a solution of 50% dimethylformamide and 50% DDW (pH 4.7)] was added to each well, and the plates were incubated again overnight at 37° C. Finally, color intensity was measured using an ELISA reader at 570 nm.

For executing the ThT florescence assay, $A\beta_{1-40}$ was dissolved to a concentration of 10 μM in 10% DMSO in PBS (pH 7.4). Aβ was immediately mixed with or without different concentrations of SY-81 or SY-83 at a 1:1 ration to a final concentration of 5 μM. The samples were incubated at 37° C. and the fibrillogenesis rate was followed by thioflavin T (ThT) fluorescence assay (excitation at 450 nm, 2.5 nm slit, and emission at 480 nm, 5 nm slit), over a course of 11 days to two weeks. ThT was added to a 10-fold diluted sample and measured using a Jobin Yvon Horiba Fluoromax 3 fluorimeter.

Samples (10 μL) from the $A\beta_{1-40}$ ThT fluorescence assay (with and without inhibitors SY-81 and SY-83) were placed on 400-mesh copper grids covered by carbon-stabilized Formvar film (SPI Supplies, West Chester, Pa.) for transmission electron microscopy. After 1.5 minutes, excess fluid was removed, and the grids were negatively stained with 10 μL of 2% uranyl acetate solution for 2 min. Finally, excess fluid was removed and the samples were viewed in a JEOL 1200EX electron microscope operating at 80 kV.

In vivo studies (fly maintenance) were performed with *Drosophila melanogaster* flies grown on a standard cornealmolasses medium and kept at 25° C. As *Drosophila* females can store sperm cells in their bodies, crosses were conducted using virgin females collected no longer than 8 hours after eclosion at 25° C. or 18 hours after eclosion at 18° C. Adult offspring (F1) from the crosses were collected up to 9 days after the beginning of their eclosion at 25° C. in order to avoid collection of offspring from the next generation (F2). Male flies carrying the driver Gal4-elav$^{c155}$ (on their X chromosome), were crossed with females carrying the $A\beta_{1-42}$ transgene (located on an autosome) under the UAS promoter in a homozygous condition. This resulted in first generation (F1) female offspring expressing $A\beta_{1-42}$ in their nervous system. They served as our Alzheimer's *Drosophila* model. Male F1 offspring, which carried the $A\beta_{1-42}$ transgene but did not express it (because they lacked the Gal4 driver) served as a control.

In order to feed the flies with an inhibitor, SY-81 dissolved DMSO and diluted in water to a concentration of 0.75 mg/mL was added to standard corneal-molasses medium about 10 minutes after cooking. The compound was well mixed into the medium and aliquoted into rearing vials. The vials were kept at 4° C. until use. Crosses were done either on regular *Drosophila* medium or on medium supplemented with SY-81. The flies were fed on the appropriate medium from the beginning of the larval stage onwards.

The following *Drosophila* strains were used: (1) y[1] f[1] X^X Gal-4-elav$^{c155}$/Y (Crowther et al., Neuroscience, 2005, vol. 132:123-135, rebalanced from a stock obtained from the Bloomington Stock center); (2) three Alz-transgenic strains kindly provided by Dr. David Gubb, Spain—(i) w; Alz[1-42.UAS]3; (ii) w; w[mC]=Alz[1-42.UAS]3; Alz[1-42.UAS]8/TM6B, Hu e Tb; and (iii) w; P{w[+mC]=Alz[Arc.UAS]}2E.

The locomotion (climbing) assay was carried out in fresh rearing vials, each containing 10 flies of a given class (four classes mentioned below). Vials were tapped gently on the table and were let stand for 18 seconds. The percent of flies which climbed to the top of the test tube was then calculated over time. Each class had six independent vial replicates. Data were analyzed using standard ANOVA statistical exams.

For the longevity assay, flies expressing one copy of $A\beta_{1-42}$ (i.e., F1 offspring, expressing one copy of $A\beta_{1-42}$, from crosses of the Alz-transgenic strains to the Gal4-elav$^{c155}$ driver strain) reared at 29° C. on medium with or without SY-81 were separated to four classes: 1. Female expressing $A\beta_{1-42}$ grown on regular medium. 2. Female expressing $A\beta_{1-42}$ grown on medium with SY-81. 3. Male controls (lacking the Gal4 driver) grown on regular medium. 4. Male controls (lacking the Gal4 driver) grown on medium supplemented with SY-81. For each class, six plastic vials each with 10 flies were collected and fresh food was given every three days (whether with or without SY-81). The number of viable $A\beta_{1-42}$ expressing and control flies with and without SY-81 was recorded daily post eclosion. Differences in survival rates were analyzed using the SPSS 11 Kaplan-Meir software package.

Example 1

Assessing Inhibition of Oligomer Formation

In Vitro Assays

Figure 2:
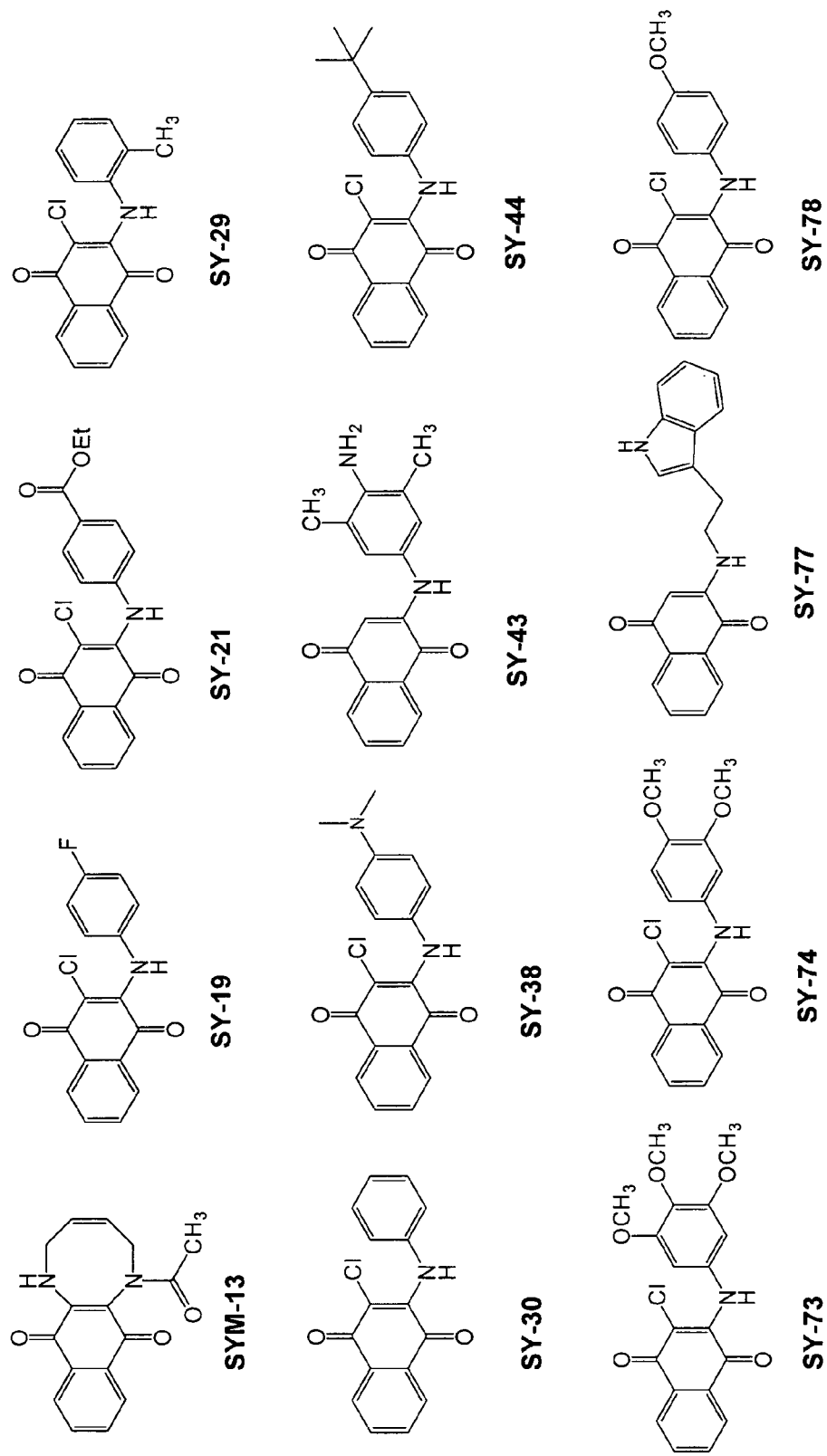
FIG. 2 depicts representative substituted naphthoquinones according to the principles of the invention.
Figure 2:
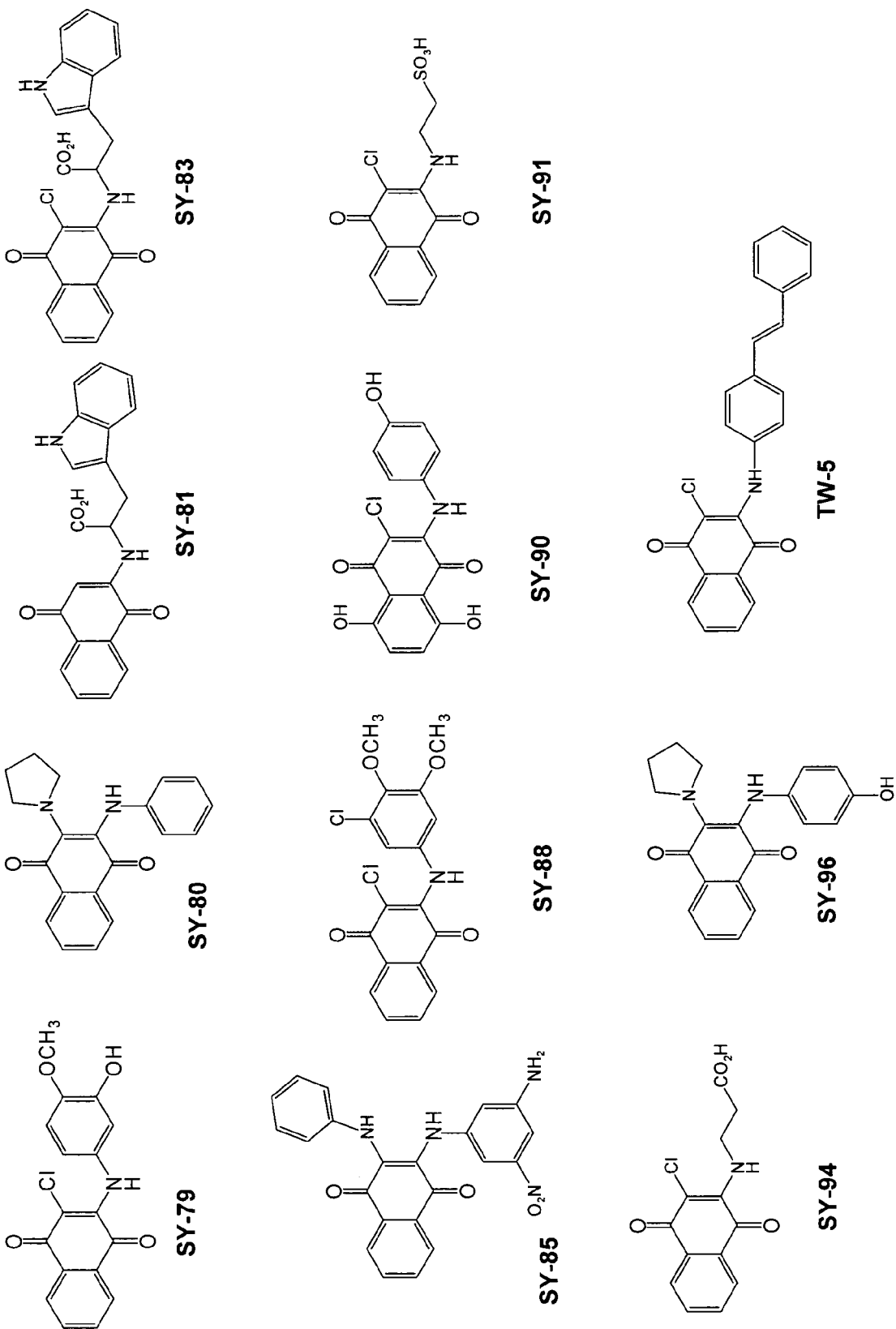

Twenty three substituted naphthoquinones (FIG. 2 and Table 1) were synthesized and analyzed for possible inhibition of formation of SDS-soluble oligomers from Aβ monomers in solution using the assay described in Barghorn (Ibid). Several substituted naphthoquinones showed notable inhibition towards formation of Aβ oligomers. Concentration dependent inhibition of Aβ oligomers was observed for several naphthoquinones screened, and the strongest inhibition was seen using two tryptophan substituted naphthoquinones, SY-81 and SY-83 (FIG. 5). The effect both SY-81 and SY-83 on the ability of early non-toxic intermediate oligomers (~18 kDa) to further grow into the larger oligomer assemblies (~56 kDa) known to be toxic is clearly evident Inhibition was seen at ratios as low as 5:1 ($A\beta_{1-42}$: quinone compound).

TABLE 1

Representative quinone derivatives

| Compound name (Formula No.) | $R^2$ | $R^3$ | $R^4$ |
|---|---|---|---|
| SY-77 (XIII) | H | (indole-ethyl structure) | H |

TABLE 1-continued
Representative quinone derivatives
| Compound name (Formula No.) | R² | R³ | R⁴ |
|---|---|---|---|
| SY-96 (XXI) |  | 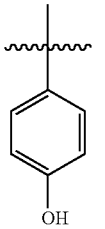 | H |
| SY-90 (XXI) | Cl | 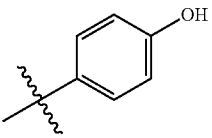 [SMILES: *c1ccc(O)cc1] | H |
| SY-80 (XVI) |  | 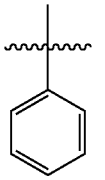 | H |
| SY-83 (XVIII) | Cl | 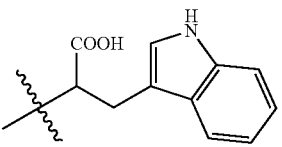 [SMILES: *C(Cc1c[nH]c2ccccc12)C(=O)O] | H |
| SY-91 (XXII) | Cl | 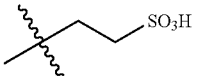 | H |
| SY-94 (XXIII) | Cl | 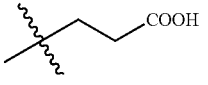 [SMILES: *CCC(=O)O] | H |
| SY-21 (V) | Cl | 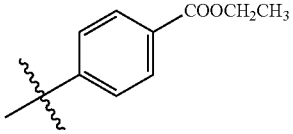 | H |
| SY-79 (XV) | Cl | 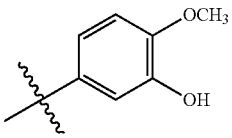 [SMILES: *c1ccc(OC)c(O)c1] | H |
| SY-19 (IV) | Cl | 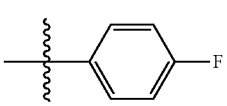 | H |
| SY-85 (XIX) | 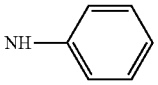 | 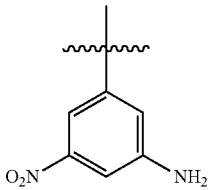 [SMILES: *c1cc(N)cc([N+](=O)[O-])c1] | H |

TABLE 1-continued
Representative quinone derivatives
| Compound name (Formula No.) | R² | R³ | R⁴ |
|---|---|---|---|
| SY-43 (IX) | H | 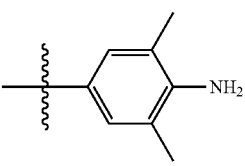 [SMILES: *c1cc(C)c(N)c(C)c1] | H |
| TW-5 (XXV) | Cl | 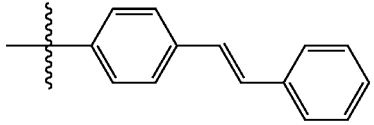 [SMILES: *c1ccc(/C=C/c2ccccc2)cc1] | H |
| SY-73 (XI) | Cl | 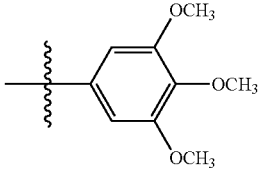 | H |
| SY-29 (VI) | Cl | 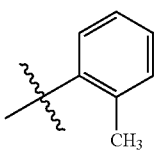 [SMILES: *c1ccccc1C] | H |
| SY-81 (XVII) | H | 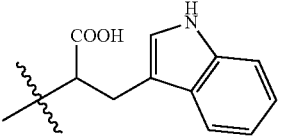 [SMILES: *C(Cc1c[nH]c2ccccc12)C(=O)O] | H |
| SY-38 (VIII) | Cl | 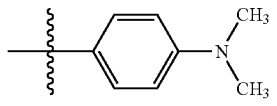 | H |
| SY-88 (XX) | Cl | 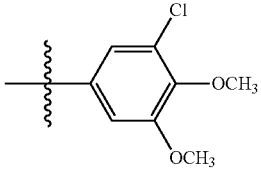 [SMILES: *c1cc(Cl)c(OC)c(OC)c1] | H |
| SY-30 (VII) | Cl | 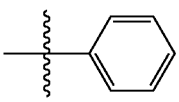 | H |
| SY-74 (XII) | Cl | 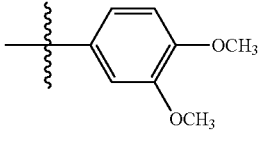 [SMILES: *c1ccc(OC)c(OC)c1] | H |
| SY-78 (XIV) | Cl | 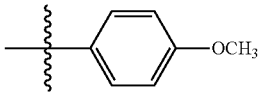 | H |

TABLE 1-continued

Representative quinone derivatives

| Compound name (Formula No.) | $R^2$ | $R^3$ | $R^4$ |
|---|---|---|---|
| SYM-13* (III) | HN-containing structure | $H_3C-C(=O)-$ group | |
| SY-44 (X) | Cl | 4-(2-methylpropan-2-yl)phenyl group (p-C(CH$_3$)$_3$-C$_6$H$_4$-) | H |

*$R^2$ and $R^4$ together form a hetero cyclic ring.
"⌇" represents the point of attachment of the particular group shown.

Figure 3A:
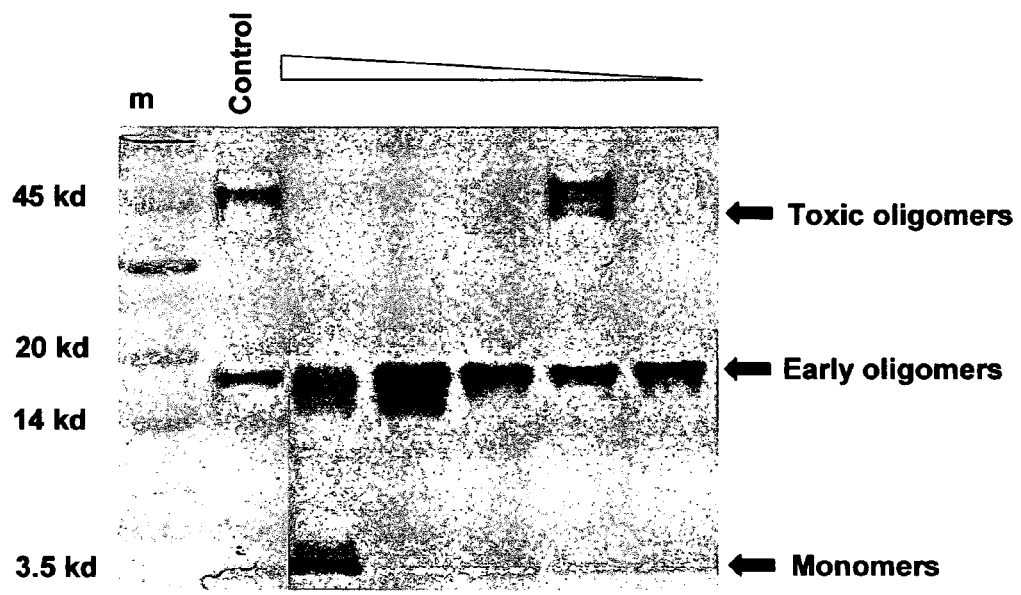
FIG. 3 exhibits concentration dependent inhibition of formation of $A\beta_{1-42}$ oligomers after incubation for 24 hours at 37° C. with Trp-substituted quinones SY-81 (A) and SY-83 (B). Left lane—size markers, control lane—$A\beta_{1-42}$ with no quinone (untreated).
Figure 3B:
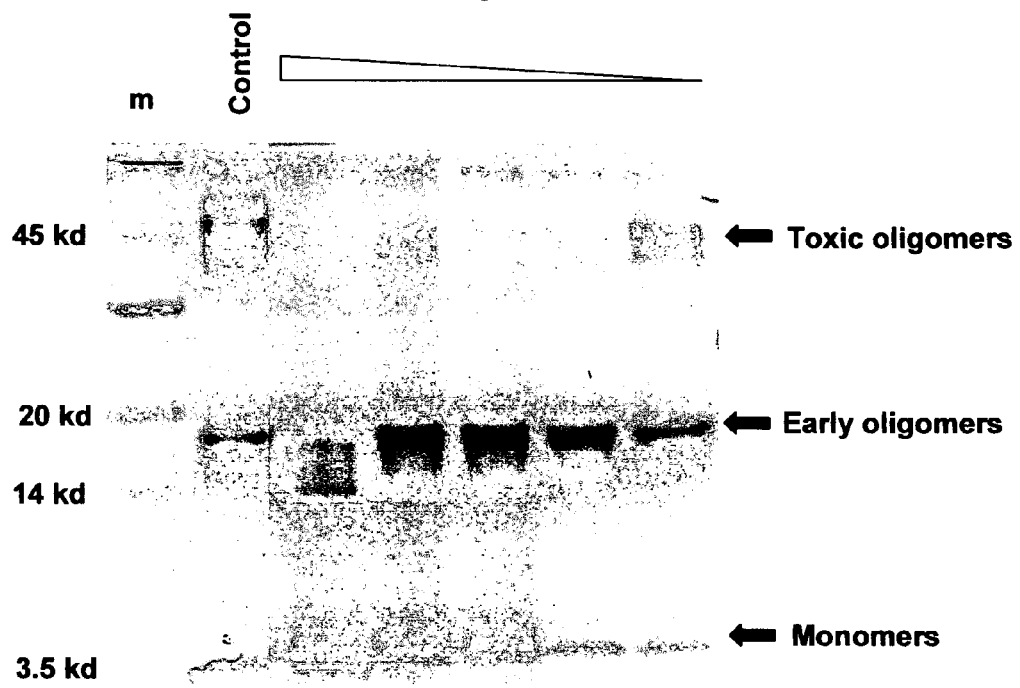

As shown in FIG. 3 the tryptophan substituted naphthoquinones SY-81 and SY-83 establish a concentration dependent inhibition of formation of $A\beta_{1-42}$ oligomers. In addition, oligomerization of $A\beta_{1-42}$ increased with decreasing concentrations of inhibitors SY-83 and SY-81. Oligomer formation after 24 hours at 37° C. in the presence of SY-81 was significantly inhibited and oligomer formation after 24 hours at 37° C. with SY-83 was significantly inhibited.

Example 2

Affinity of Inhibitors to $A\beta$

Figure 4A:
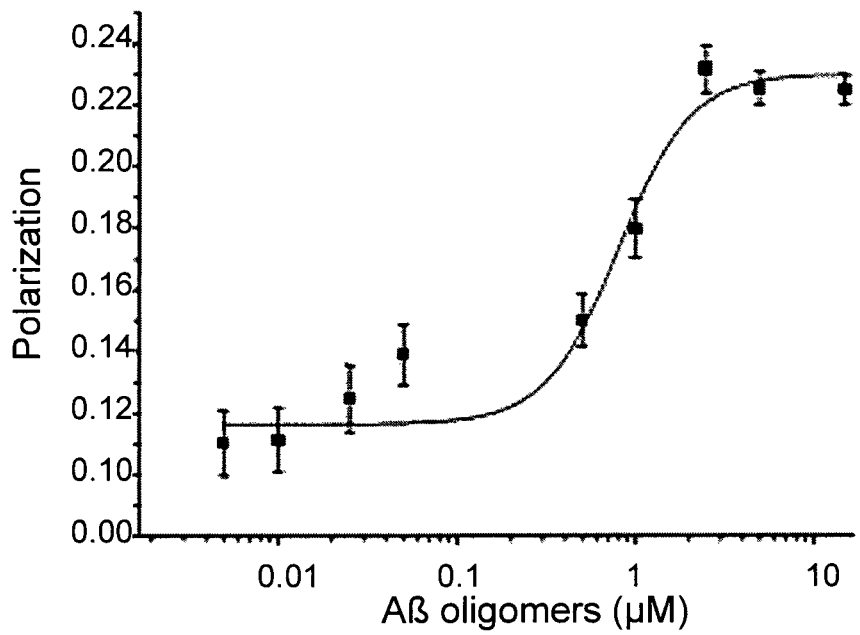
FIG. 4 presents the affinity of tryptophan naphthoquinones towards Aβ through the binding of the inhibitors SY-83 (A) and SY-81 (B) to Aβ as monitored by following their fluorescence polarization upon titration with $A\beta_{1-42}$ solution.
Figure 4B:
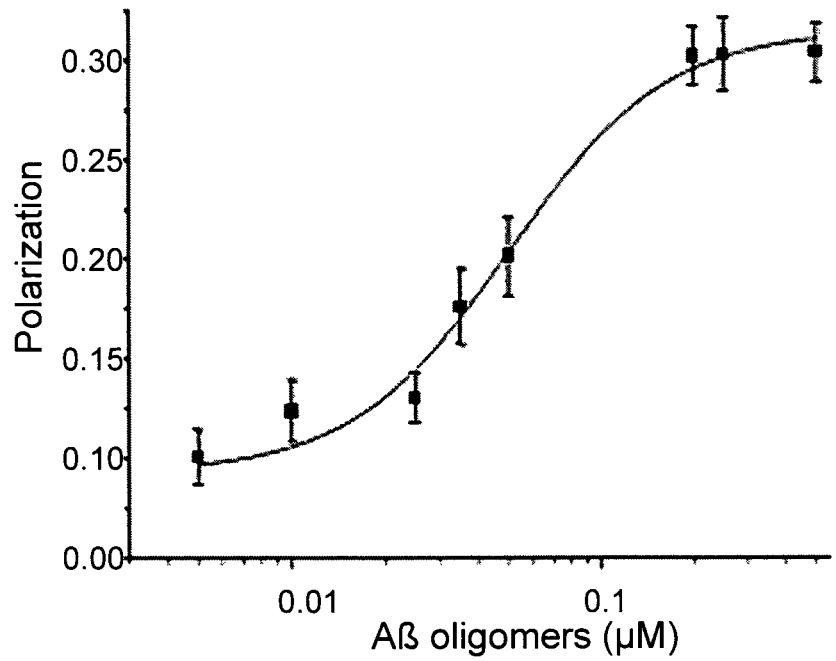
Figure 5A:
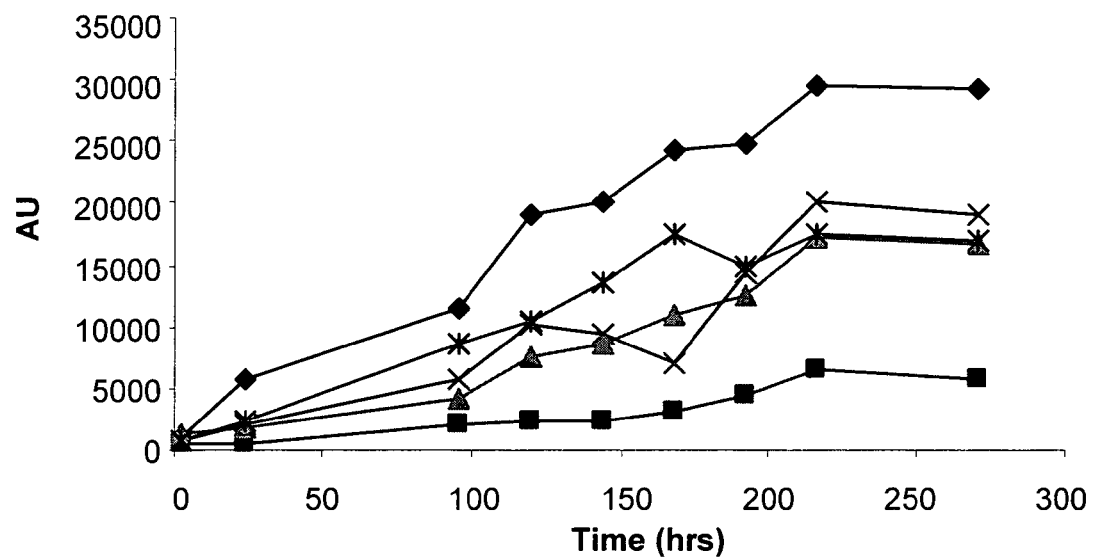
FIG. 5 shows the concentration dependent inhibition of $A\beta_{1-40}$ fibrils (5 μM; concentration indicated as quinones:Aβ molar ratio) using the Thioflavin T (ThT) florescence assay expressed in arbitrary units with different concentrations of SY-83 (diamond-WT, x-1:2, square-5:1, *-1:4, triangle-1:1) over the course of 270 hrs (A, B) or with different concentrations of SY-81 (diamond-WT, x-1:2, square-5:1, *-1:4, triangle-1:1) over the course of 270 hrs (C, D).
Figure 5B:
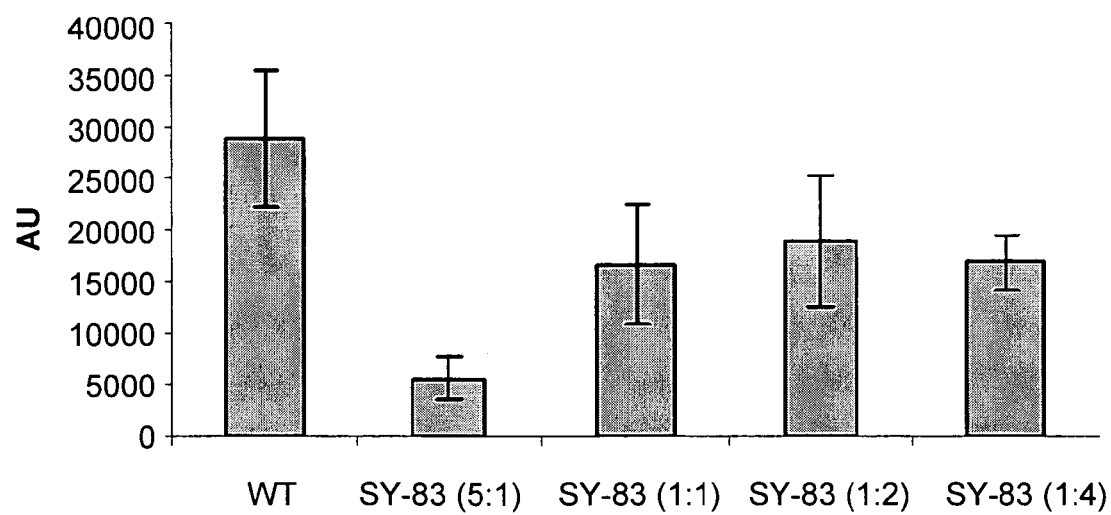
Figure 5C:
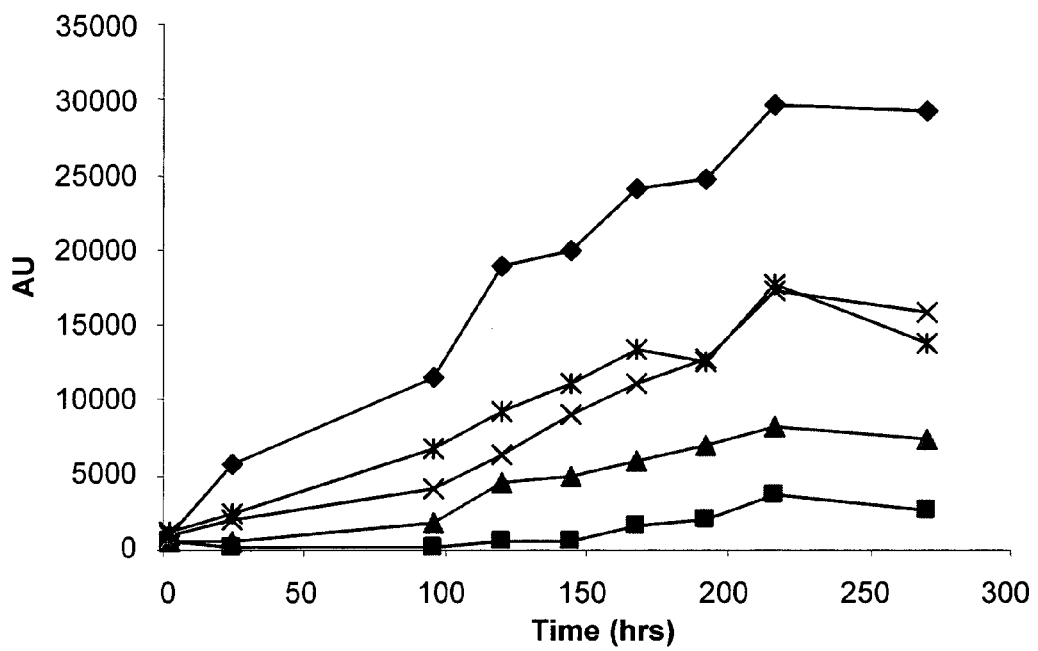
Figure 5D:
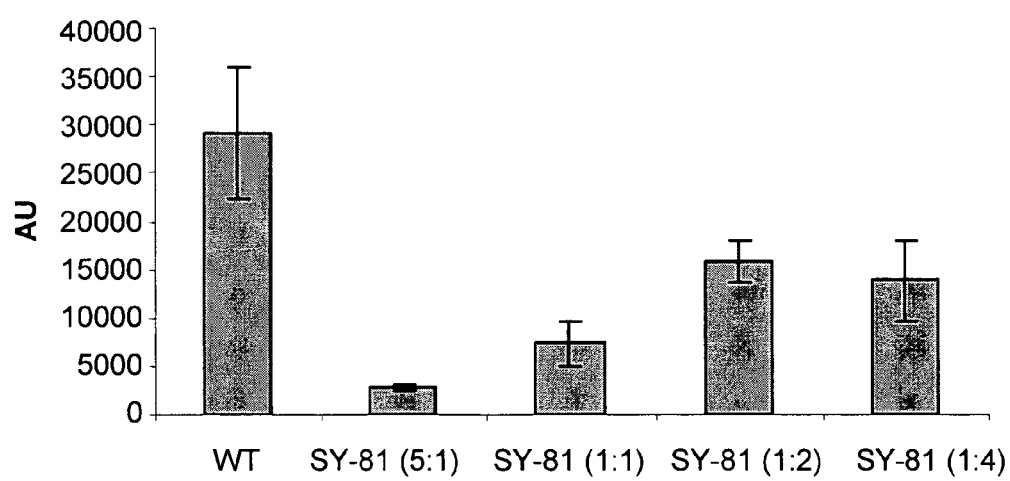

The affinity of SY-83 and SY-81 towards the $A\beta$ was demonstrated using fluorescence anisotropy experiments, taking advantage of the intrinsic fluorescence of the two Trp-substituted quinones and their relatively small size as compared to the $A\beta$ oligomers. Increasing amounts of $A\beta$ were titrated into a solution of SY-83 or SY-81 and the anisotropy was determined (FIG. 4). The affinity of SY-83 and SY-81 was found to be about 900 nM and 90 nM, respectively.

Example 3

Inhibition of $A\beta$ Fibril Formation

Though there is a growing recognition that the early $A\beta$ oligomer intermediates and not the fibrils are the most toxic amyloid forms in AD, this debate has not been completely resolved. To discern whether Trp-substituted quinones also inhibit the formation of mature $\beta$-amyloid fibrils, the Thioflavin-T (ThT) binding assay was applied. This method provides quantitative information on amyloid fibrils growth. $\beta$-amyloid was allowed to form amyloid fibrils either in the presence of different concentrations of SY-83 (FIG. 5A, C) or SY-81 (FIG. 5 B, D) or with no inhibitor (WT). The fibrillization process was followed for several days until a plateau state was reached. Fluorescence values were measured throughout. The formation of amyloid fibrils was significantly lowered in the presence of the inhibitors, even at very low concentrations such as 1.25 μM, as observed by fluorescence intensity. These results clearly indicate that SY-81 and SY-83 have high potential as inhibitors of $\beta$-amyloid fibril formation.

An end point experiment was further conducted with various concentrations of SY-81 and SY-83 in order to determine $IC_{50}$. An $IC_{50}$ of 50 nM and 100 nM was measured for SY-81 and SY-83, respectively. It is noted that his value is much lower than the corresponding value of other naphthoquinone derivatives known in the art.

Example 4

Morphology of Fibril Inhibition

Figure 6A:
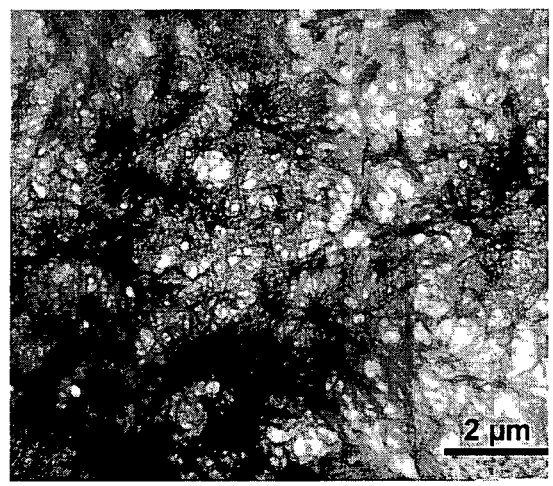
FIG. 6 presents transmission electron microscope (TEM) images of $A\beta_{1-40}$ fibrils (5 μM), taken at T=270 hrs untreated (WT, A) and treated with SY-81 (25 μM, B) or with SY-83 (25 μM, C).
Figure 6B:
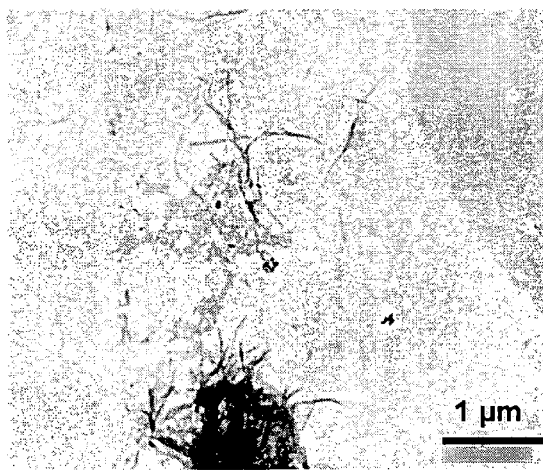
Figure 6C:
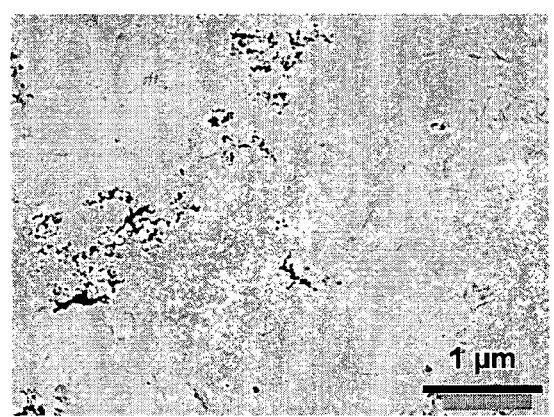

The morphology of the $\beta$-amyloid fibrils formed, with and without the inhibitors, was assessed during the course of the fibrillization assay. This was done using transmission electron microscopy (TEM), one of the most direct methods for the detection of amyloid fibrils. TEM imaging allows direct visualization of the fibrillar nature of the aggregates at high resolution. The occurrence and characteristic of the amyloid fibrils were therefore studied by TEM using negative staining with 2% uranyl acetate. Samples were taken from the kinetic experiment (shown in FIG. 6) after 7 days of incubation. Large fibrillar structures were observed for $A\beta$ alone in contrast to samples of $A\beta$ with either inhibitor, SY-81 or SY-83, which showed a marked inhibition in fibril formation (FIGS. 6 A, B and C, respectively). This strongly correlates with the values obtained by the ThT inhibition experiment (FIG. 5). The fibrils formed by the $A\beta$ alone were large, broad and ribbon-like (FIG. 6A). The fibrils seen in the presence of the inhibitors were much thinner and shorter compared to the fibrils formed by the $A\beta$ protein alone, and were less abundant (FIG. 6B, C). Thus, both compounds not only inhibit formation of the oligomeric structures but also of the larger fibrillar structures.

Example 5

Fibril Inhibition in Cultured Cells

Figure 7A:
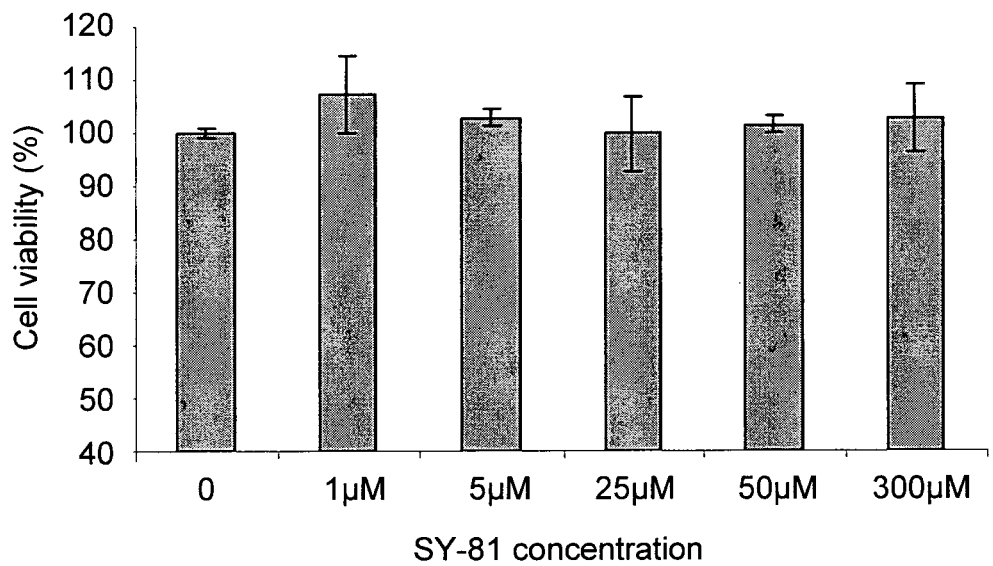
FIG. 7 exhibits the effect of SY-81 on cytotoxicity of soluble Aβ oligomers towards rat PC12 cell culture pre-incubated with different concentrations of SY-81 for 24 hours. Cell viability was determined using MTT cell viability assay in cells exposed to SY-81 (A) or to soluble oligomers pre-incubated with increasing amounts of SY-81 (B).
Figure 7B:
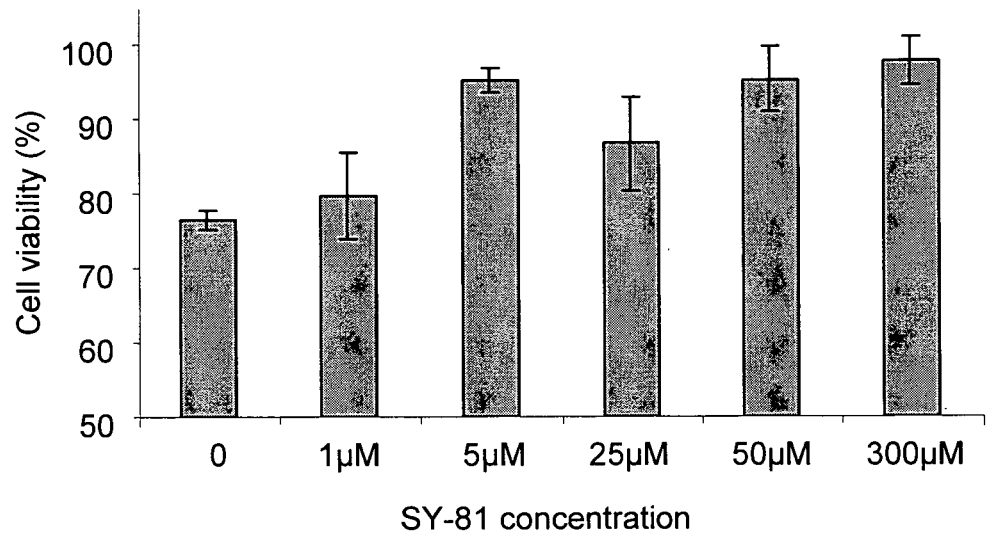

To further substantiate the inhibition induced by SY-81, it was tested whether SY-81 affects the toxicity of $A\beta$ oligomers towards the rat PC12 cell line. Toxic oligomers were pre-incubated with different concentrations of SY-81 and toxicity was assessed using the MTT cell viability assay. While showing no toxic effect of its own (FIG. 7A), SY-81 was found to significantly inhibit the toxic effect of $A\beta$ towards the cultured cells (FIG. 7B).

Example 6

Fibril Inhibition in the Living Organism

In order to assess the effect of SY-81 and SY-83 in the living organism, a *Drosophila* model of Alzheimer's was used, based on the work of Crowther et al. (ibid) who generated transgenic flies that express the human Aβ$_{1-42}$ protein conditionally, using the UAS-Gal4 expression system. Crowther et al. showed that flies expressing the Aβ$_{1-42}$ in the nervous system (using the pan-neural Gal-4-elav$^{c155}$ driver) exhibit defects reminiscent of Alzheimer's. These defects included progressive decline of locomotion in aged flies (measured as ability to climb up), and marked shortening of life span.

We crossed male flies carrying the driver Gal-4-elav$^{c155}$ (on their X chromosome) to females carrying the Aβ$_{1-42}$ transgene under the UAS promoter in a homozygous condition. This resulted in first generation (F1) female offspring expressing Aβ$_{1-42}$ in their nervous system, which served as the Alzheimer's Drosophila model. Male F1 offspring, which carried the Aβ$_{1-42}$ transgene but did not express it (because they lacked the Gal4 driver) served as a control. This cross was performed either on regular Drosophila medium or on medium supplemented with 0.75 mg/ml SY-81. The animals fed on the appropriate medium from the beginning of the larval stage onwards.

Figure 8A:
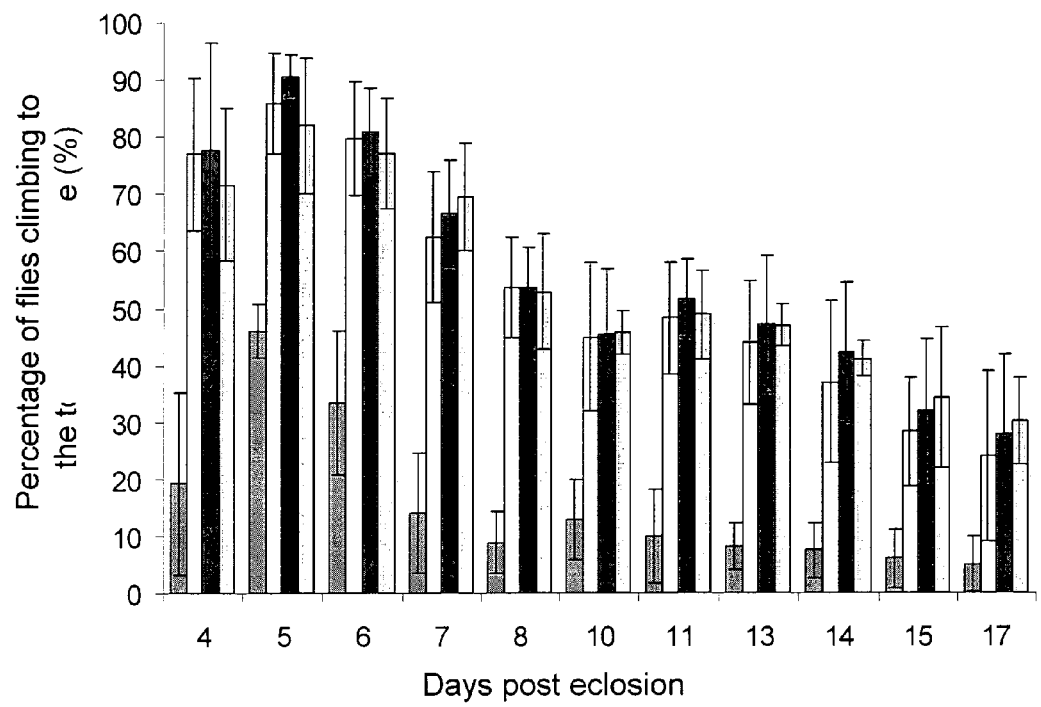
FIG. 8A depicts the effect of SY-81 on the climbing behavior (to the top of a test tube) of flies expressing $A\beta_{1-42}$ in their nervous system (genotype: Gal4-elav$^{c155}$ UAS-$A\beta_{1-42}$ treated or untreated with SY-81 the two bars on the left side in each group of four represent females expressing $A\beta_{1-42}$ without (dark gray) or with (light gray) SY-81, respectively), compared with age-matched control flies (males of the Gal4-elav$^{c155}$ driver line) which were grown on medium with and without SY-81 (the two bars on the right of each group of four represent control males flies without (dark gray) and with (light gray) SY-81, respectively). $p<0.00001$ for $A\beta_{1-42}$-expressing females grown on regular medium compared to AD females grown on SY-81 and to both control males.
Figure 8B:
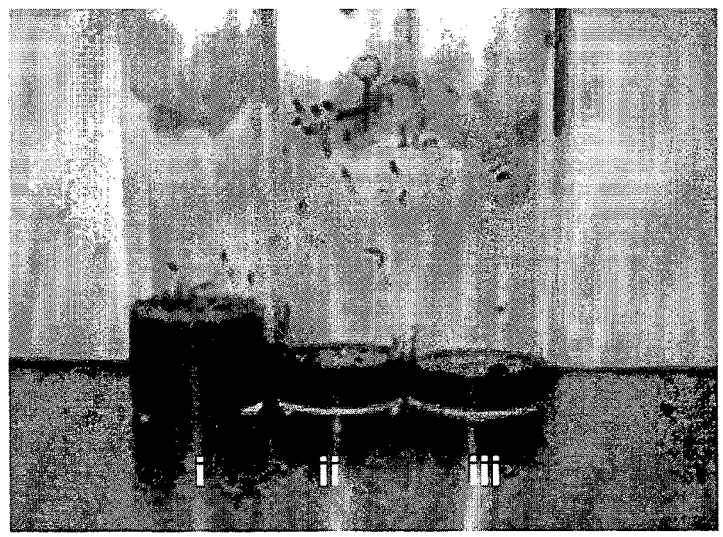
FIG. 8B shows images of $A\beta_{1-42}$-expressing fly females untreated (i), treated with SY-81 (ii), or control male flies (iii).

Suppression of climbing defects was assessed as detailed below in flies genotype: Gal-4-elav$^{c155}$ UAS-Aβ$_{1-42}$. Aβ$_{(1-42)}$-expressing flies behaved normally at eclosion from the pupal case and subsequently developed locomotion deficits as reported by Crowther et al (ibid). At four days after eclosion the Alzheimer's-expressing flies showed a marked decrease in their normal fly climbing behavior. Each class of flies examined (male control flies grown on regular medium, male control flies grown on medium containing SY-81, females expressing Aβ$_{1-42}$ grown on regular medium and females expressing Aβ$_{1-42}$ grown on SY-81) was analyzed in a climbing assay. Control flies (males of the Gal4-elav$^{c155}$ driver line) were grown on medium with and without SY-81. Fresh rearing vials, each containing 10 flies of a given class, were tapped gently on the table and were let stand for 18 seconds. The percent of flies, for each group of treatment (SY-81 or control) which climbed to the top of the test tube was then calculated (FIG. 8A). Each class had six independent rearing vial repeats. Female flies expressing the Aβ$_{1-42}$ transgene grown on regular medium showed accelerated decline in climbing behavior, becoming almost immobile by day 15, as previously reported (Crowther et al.; ibid). In contrast, females expressing the Aβ$_{1-42}$ transgene grown on medium containing SY-81 showed dramatic improvement, behaving almost identical to the control classes (males without SY-81). No effect of SY-81 was observed on the control males.

Example 7

Suppression of Longevity Defects

Figure 9A:
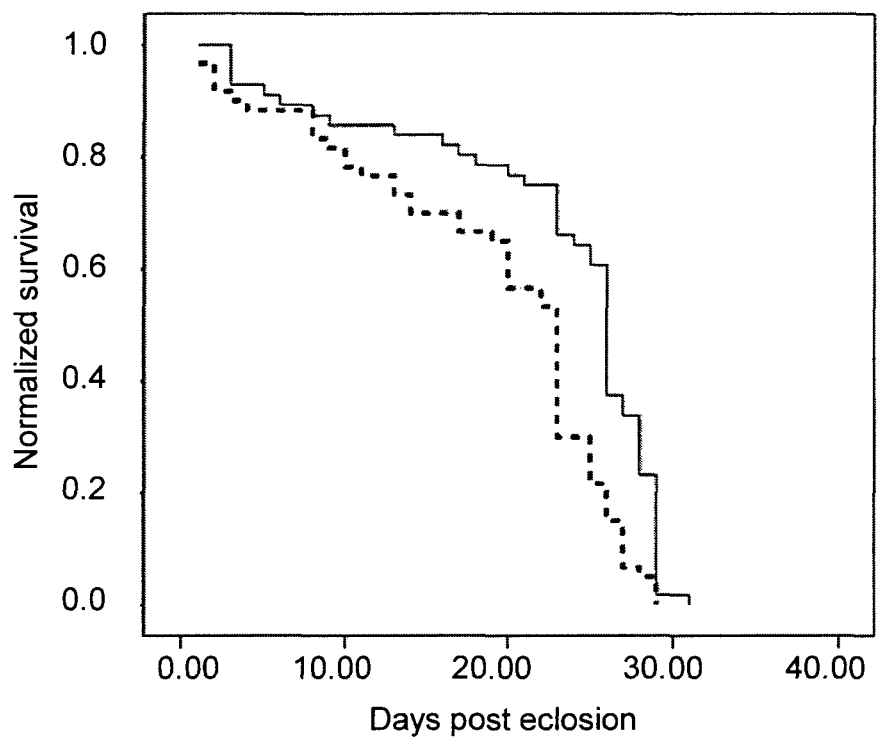
FIG. 9A presents the effect of SY-81 on survival of flies expressing $A\beta_{1-42}$ in their nervous system (genotype: Gal-4-elav$^{c155}$ UAS-$A\beta_{1-42}$; hatched line) and $A\beta_{1-42}$-expressing females which were grown on medium with SY-81 (solid line), $p<0.0001$.
Figure 9B:
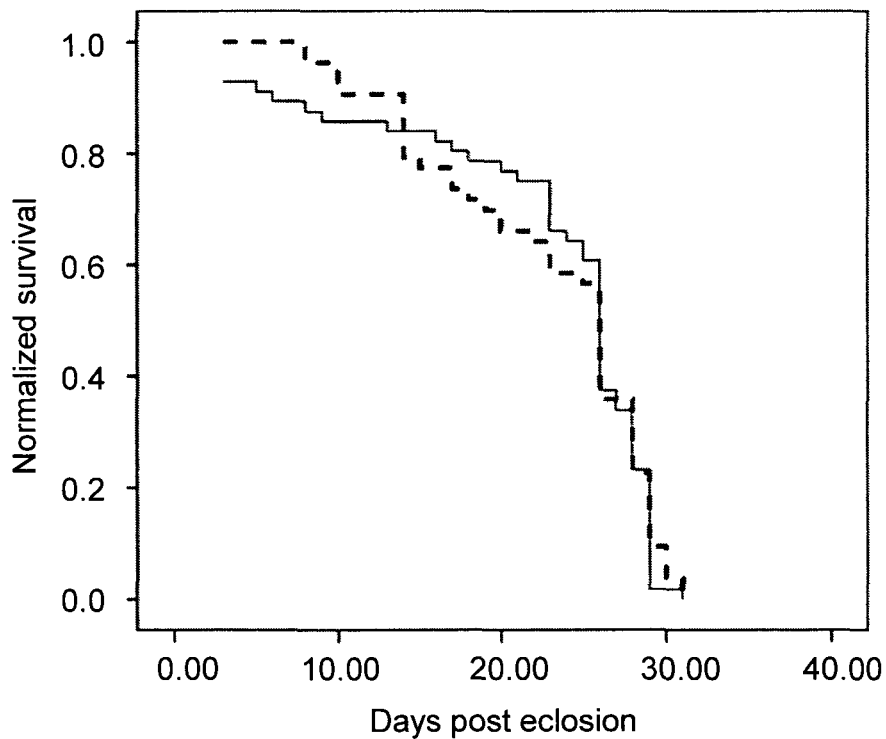
FIG. 9B exhibits the survival of control flies (males of the Gal4-elav$^{c155}$ driver line, solid line) grown on SY-81 and $A\beta_{1-42}$-expressing females which were grown on medium with SY-81 (hatched line), $p>0.05$.
Figure 9C:
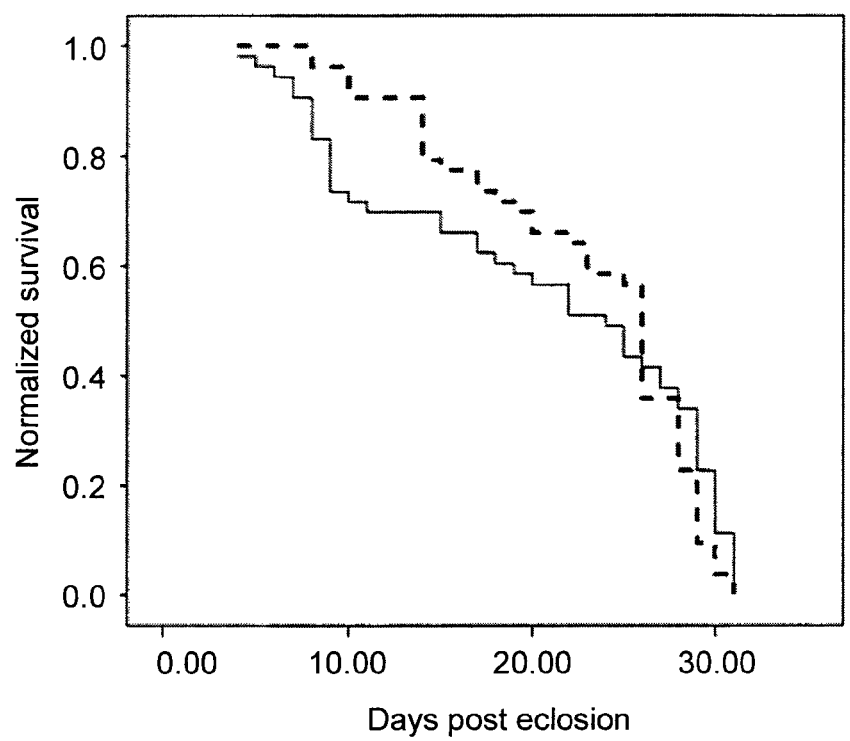
FIG. 9C provides the survival of control flies (males the Gal4-elav$^{c155}$ driver line, solid line) grown on SY-81 compared to control flies (males of the Gal4-elav$^{c155}$ driver line, hatched line) grown on regular medium. $p>0.05$.

A longevity assay on the four classes of flies described in the above example, was performed. It has been known that expression of Aβ$_{1-42}$ in Drosophila flies causes a marked reduction in survival (Crowther et al.; ibid). Indeed, females expressing the Aβ$_{1-42}$ transgene grown on regular medium showed a statistically significant reduction in their life span as compared to females expressing the Aβ$_{1-42}$ transgene grown on medium containing SY-81 (0.75 mg/ml) (FIG. 9B). Remarkably, survival of females expressing the Aβ$_{1-42}$ transgene grown on medium containing SY-81 was nearly identical to that of control male controls grown on SY-81 (FIG. 9C) or of male controls grown on regular medium.

Example 8

The Inhibitory Effect of the SY-83 Compound in AD Model Mice

Figure 10:
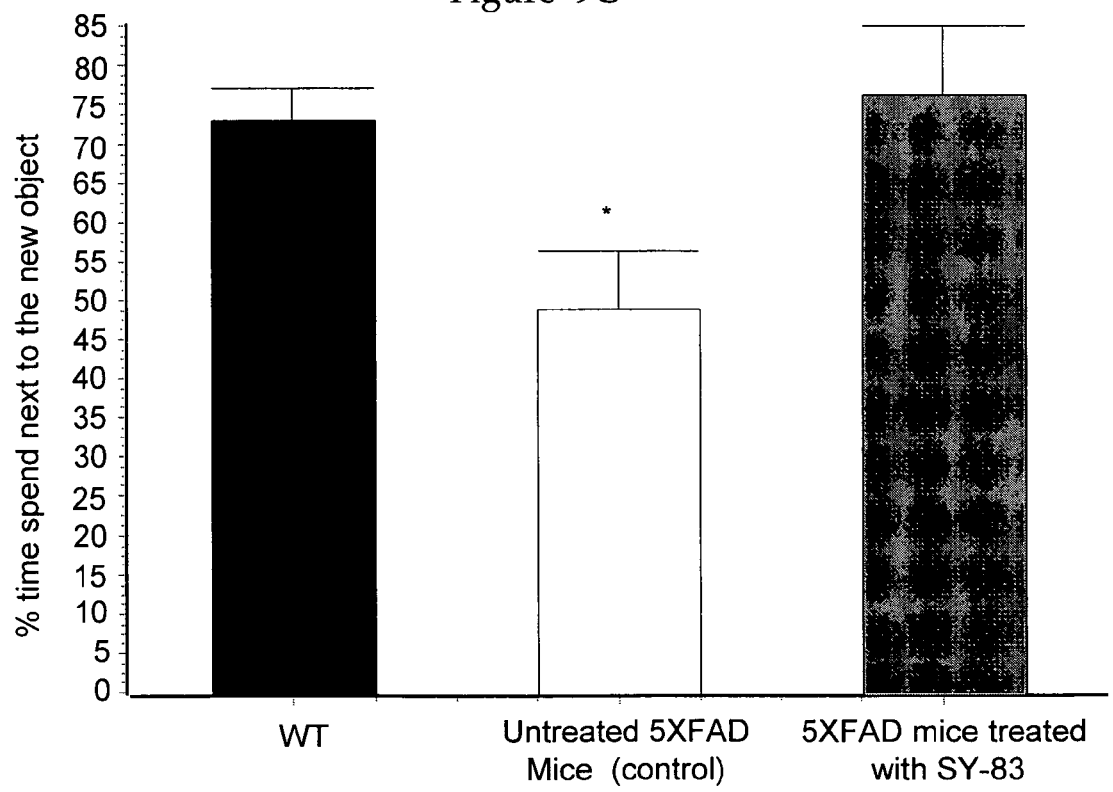
FIG. 10 presents the results of an object recognition test of WT mice, 5×FAD mice treated with the SY-83 molecule and untreated 5×FAD mice (control).
Figure 11A:
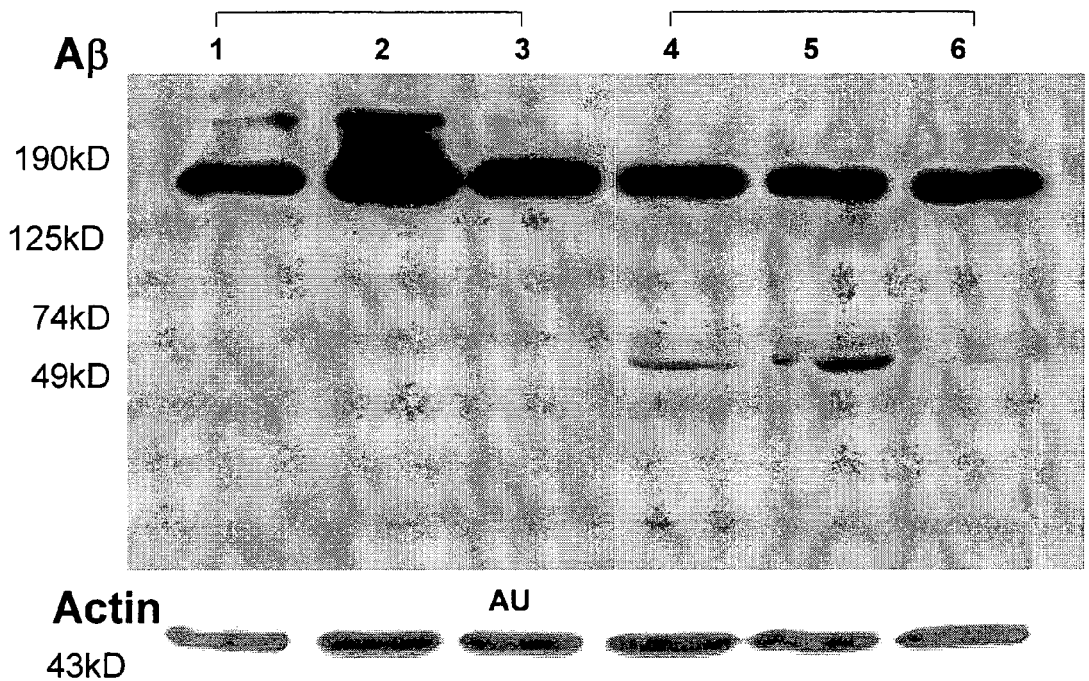
FIG. 11 shows a soluble fraction of brains of untreated 5×FAD mice (lanes 4-6) and 5×FAD mice treated with SY-83 (lanes 1-3) analyzed by SDS-PAGE gel and probed with a specific Aβ antibody, 6E10 (A) and the corresponding statistics for three mice of each type (B) two tail $p<0.05$, one tail $p<0.005$.
Figure 11B:
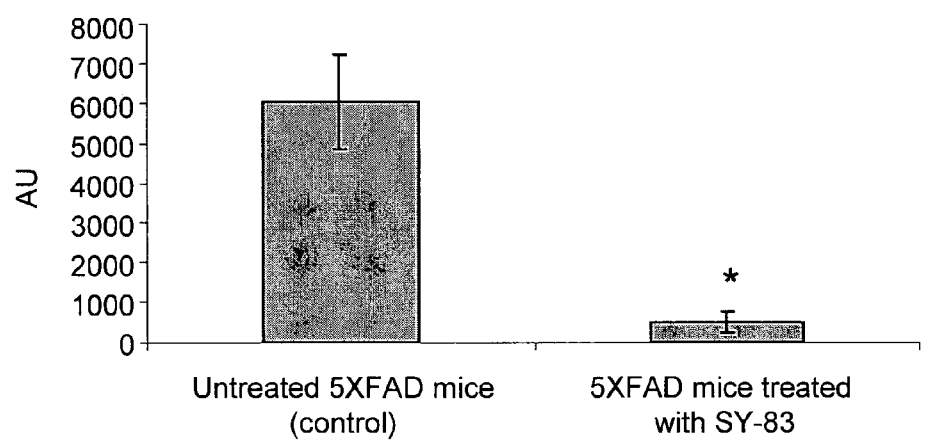

The effect of one of the quinone-based compounds, SY-83, was studied in vivo in AD mice model. The mice in this AD model co-express a total of five familial AD (FAD) mutations ("5xFAD"), driven by the neuron-specific Thy 1 promoter (Lesne et al., Nature, 2006, vol. 440:352-357. These "5XFAD" mice exhibit AD symptoms at younger age than AD mice harboring fewer FAD mutations. For example, 5xFAD mice develop cerebral amyloid plaques and gliosis already at 2 months of age, achieve massive Aβ burdens. They have reduced synaptic markers, exhibit neuron loss, a fundamental characteristic of AD lacking in most AD transgenic models, and display memory impairment in the Y-maze. Two months old 5xFAD mice were injected, every other day, intraperitoneally with either 1 mg of SY-83 in PBS for a period of 4 months. Control mice were injected with PBS for the same period of time. At that age they, as well as untreated wild type non transgenic littermates control mice, were subjected to a standard cognitive test (an object recognition test; Bevins and Besheer, Nat. Protoc. Vol. 1(3): 1306-1311, 2006). The results are shown in FIG. 10. In brief, mice were placed in an apparatus for 5 minutes. In the next day (24 hrs later) mice were placed in the same apparatus but this time an object was added and was allowed to be explored for 5 minutes. After 24 h, the mice were returned to the apparatus, which now contains the familiar object and a novel object. Object recognition is distinguished by a longer time spent interacting with the novel object as compared to the time spent with a familiar object. It was now found that 5xFAD mice treated with SY-83, spent significantly more time (p<0.05) exploring the novel object than control 5xFAD mice treated with PBS (FIG. 10). These results suggest that treatment with SY-83 aimed at reducing Aβ assembly can improve cognition. Indeed, western blot analysis (FIG. 11A) of soluble brain fractions from the SY-83 treated 5xFAD mice revealed 91% reduction in a 56 KD Aβ species. The 56 KD Aβ species was implicated in memory impairment and cognitive deficits in AD (Lesne et al.).

It will be appreciated by persons skilled in the art that the present invention is not limited by what has been particularly shown and described herein above. Rather the scope of the invention is defined by the claims that follow.

The invention claimed is:
1. A method for treating a disease selected from Alzheimer's Disease and dementia in an individual in need thereof, comprising administering to the individual in need thereof an effective amount of a substituted 3-amino-1,4-naphthoquinone represented by the structure of the general formula (I):

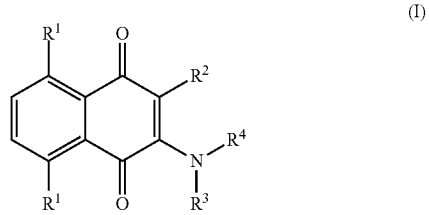

wherein
- each $R^1$ independently is selected from the group consisting of H and OH;
- $R^2$ is selected from the group consisting of H, a halogen, —$NR^5R^6$ wherein $R^5$ and $R^6$ are selected from the group consisting of H, a saturated or unsaturated cyclic moiety comprising from 5 to 8 atoms, an unsubstituted or substituted aryl and $NR^5R^6$ wherein $R^5$ and $R^6$ together form a saturated or unsaturated hetero cyclic ring comprising from 5 to 8 atoms;
- $R^3$ comprises a heterocyclic amino acid side chain selected from the group consisting of tryptophan, histidine and proline and
- $R^4$ is H;
- or $NR^3R^4$ is an amino acid residue.

2. The method of claim 1 wherein $NR^3R^4$ is an amino acid residue.

3. The method of claim 2 wherein the amino acid is selected from a group consisting of a heterocyclic amino acid and an aromatic amino acid.

4. The method of claim 3 wherein the amino acid is selected from the group consisting of tryptophan, tyrosine, histidine, proline and phenylalanine.

5. The method of claim 4 wherein the amino acid is tryptophan.

6. The method of claim 1, wherein $R^3$ comprises a heterocyclic amino acid side chain selected from the group consisting of tryptophan, histidine and proline, and $R^4$ is H.

7. The method of claim 6, wherein $R^3$ comprises the the side chain of tryptophan.

8. The method of claim 1, wherein said compound is administered in a pharmaceutical composition comprising said compound of formula (I) as an active ingredient and a pharmaceutically acceptable diluent, excipient or carrier.

9. The method of claim 1, wherein the disease is Alzheimer's Disease.

10. The method of claim 1, wherein the disease is dementia.

11. The method of claim 1, which comprises reducing memory impairment associated with Alzheimer's Disease or dementia in an individual or reducing the loss of cognitive functioning associated with Alzheimer's Disease or dementia.

12. A method for preventing or treating a disease selected from Alzheimer's Disease and dementia in an individual in need thereof, comprising administering to the individual an effective amount of a substituted 3-amino-1,4-naphthoquinone of any of the structures of formulae III-XII, XIV-XVI and XIX-XXV:

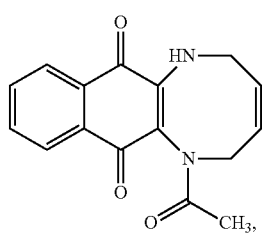
III

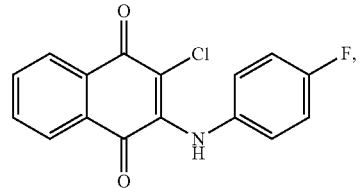
IV

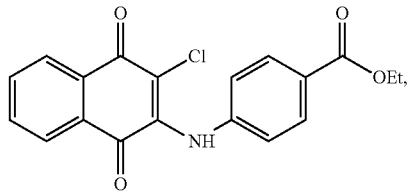
V

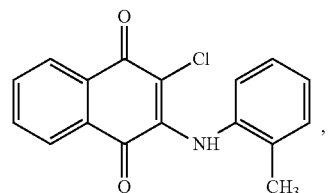
VI

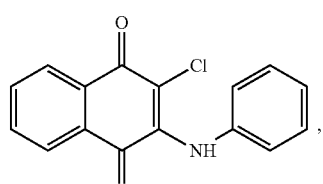
VII

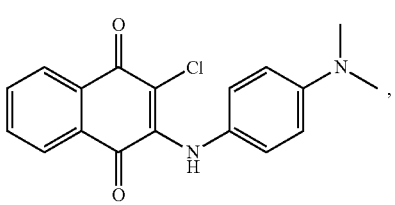
VIII

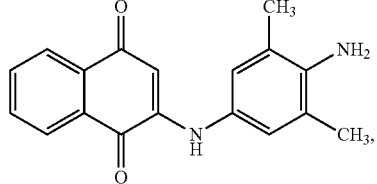
IX

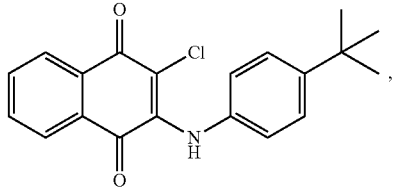
X

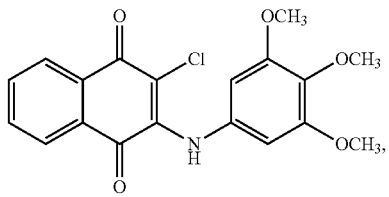
XI

XII
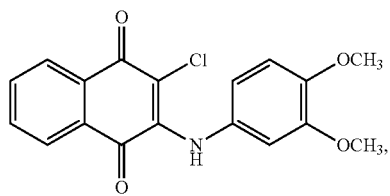

XIV
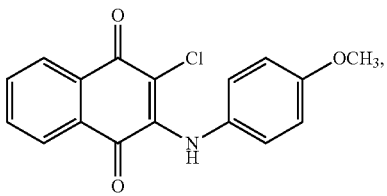

XV
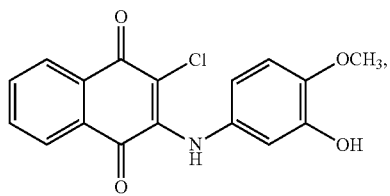

XVI
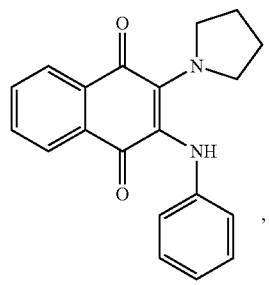

XIX
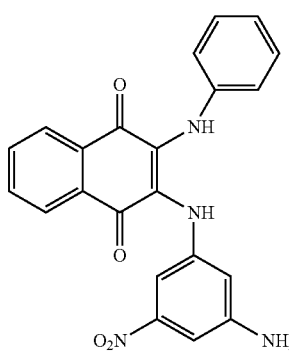

XX
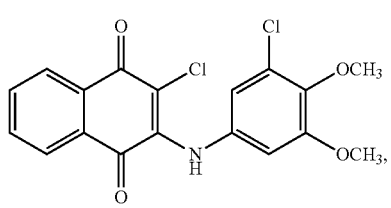

XXI
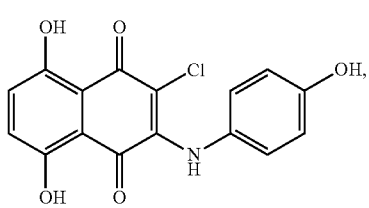

XXII
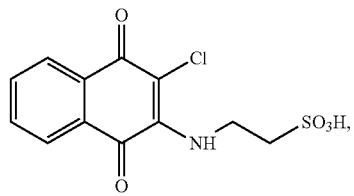

XXIII
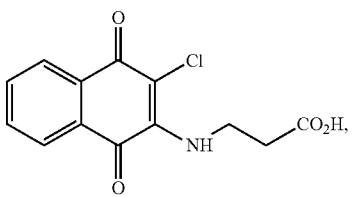

XXIV
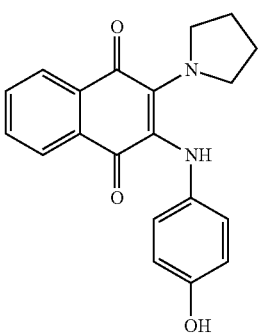

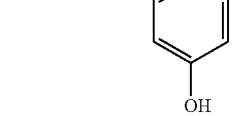
and

XXV
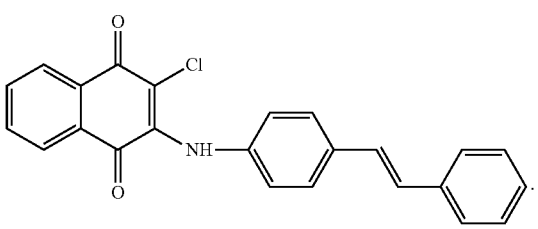

13. The method of claim 12, wherein said compound is administered in a pharmaceutical composition comprising said compound of any of formulae III-XII, XIV-XVI and XIX-XXV as an active ingredient and a pharmaceutically acceptable diluent, excipient or carrier.

14. The method of claim 12, wherein the disease is Alzheimer's Disease.

15. The method of claim 14, wherein the disease is dementia.

16. The method of claim 12, which comprises reducing memory impairment associated with Alzheimer's Disease or dementia in an individual, reducing the loss of cognitive functioning associated with Alzheimer's Disease or dementia.

17. The method according to claim 1, wherein the substituted 3-amino-1,4-naphthoquinone is represented by the structure of formula XVII

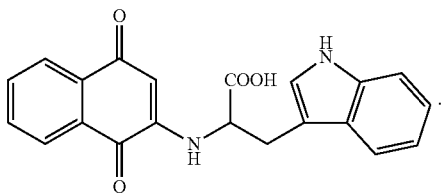
XVII
18. The method according to claim 1, wherein the substituted 3-amino-1,4-naphthoquinone is represented by the structure of formula XVIII
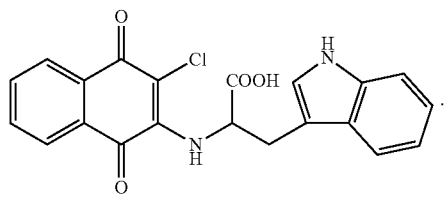
XVIII
19. The method according to claim 1, wherein the substituted 3-amino-1,4-naphthoquinone is represented by the structure of formula XIII
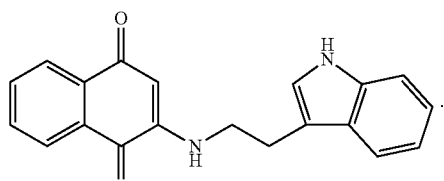
XIII
\* \* \* \* \*

UNITED STATES PATENT AND TRADEMARK OFFICE
CERTIFICATE OF CORRECTION

PATENT NO.        : 8,697,680 B2                                              Page 1 of 1
APPLICATION NO.   : 13/062067
DATED             : April 15, 2014
INVENTOR(S)       : Scherzer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 90 days.

Signed and Sealed this

Twenty-ninth Day of September, 2015

Michelle K. Lee
*Director of the United States Patent and Trademark Office*